(12) United States Patent
Bissonnette et al.

(10) Patent No.: US 6,960,142 B2
(45) Date of Patent: *Nov. 1, 2005

(54) GOLF CLUB HEAD WITH A HIGH COEFFICIENT OF RESTITUTION

(75) Inventors: Laurent C. Bissonnette, Portsmouth, RI (US); Nicholas M. Nardacci, Bristol, RI (US); Raymond L. Poynor, Oceanside, CA (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/425,881

(22) Filed: Apr. 30, 2003

(65) Prior Publication Data

US 2003/0199334 A1 Oct. 23, 2003

Related U.S. Application Data

(63) Continuation of application No. 09/551,771, filed on Apr. 18, 2000, now Pat. No. 6,605,007.

(51) Int. Cl.[7] ............................................. A63B 53/04
(52) U.S. Cl. ..................... 473/329; 473/345; 473/349
(58) Field of Search ................ 473/290, 291, 473/324, 329, 332, 342, 345, 346, 349, 350

(56) References Cited

U.S. PATENT DOCUMENTS

| | | | |
|---|---|---|---|
| 1,318,325 A | 10/1919 | Klin | |
| 1,319,233 A | 10/1919 | Mattern | |
| 1,467,435 A | 9/1923 | Kinnear | |
| 1,525,352 A | 2/1925 | Aitken | |
| 1,543,691 A | 6/1925 | Beat | |
| 1,582,836 A | 4/1926 | Link | |

(Continued)

FOREIGN PATENT DOCUMENTS

| | | |
|---|---|---|
| CN | 1114911 | 1/1996 |
| GB | 2268693 A | 1/1994 |
| GB | 2331938 A | 6/1999 |
| JP | 59207169 | 11/1984 |
| JP | 61033682 | 2/1986 |
| JP | 61162967 | 7/1986 |
| JP | 61181477 | 8/1986 |
| JP | 61185281 | 8/1986 |
| JP | 61240977 | 10/1986 |
| JP | 1244770 | 9/1989 |
| JP | 02130519 | 5/1990 |

(Continued)

OTHER PUBLICATIONS

Golf Digest, Sep., 1982, p. 25.

(Continued)

Primary Examiner—Sebastiano Passaniti
(74) Attorney, Agent, or Firm—Swindler Berlin LLP

(57) ABSTRACT

The present invention relates to a golf club head provided with a face and a body. The face has a central zone and a intermediate zone adjacent and surrounding the central zone. The central zone has a first flexural stiffness and the intermediate zone has a second flexural stiffness. The club head face is configured and dimensioned such that the first flexural stiffness is significantly greater than the second flexural stiffness such that upon ball impact with the face, the intermediate zone exhibits substantial deformation so that the central zone moves into the club head. At the same time, the central zone exhibits minimal deformation so that it moves into and out of the club head as a unit. Furthermore, the face exhibits a high coefficient of restitution.

28 Claims, 10 Drawing Sheets

U.S. PATENT DOCUMENTS

| | | |
|---|---|---|
| 1,589,363 A | 6/1926 | Butchart |
| 1,595,589 A | 8/1926 | Tyler |
| 1,605,551 A | 11/1926 | Mattern |
| 1,699,874 A | 1/1929 | Buhrke |
| 1,704,119 A | 3/1929 | Buhrke |
| 1,704,165 A | 3/1929 | Buhrke |
| 1,720,867 A | 7/1929 | Webster et al. |
| 2,034,936 A | 3/1936 | Barnhart |
| 2,087,685 A | 7/1937 | Hackney |
| 3,567,228 A | 3/1971 | Lynn |
| 3,571,900 A | 3/1971 | Hardesty |
| 3,625,518 A | 12/1971 | Solheim |
| 3,659,855 A | 5/1972 | Hardesty |
| 3,863,932 A | 2/1975 | Lezatte |
| 3,985,363 A | 10/1976 | Jepson et al. |
| 4,023,802 A | 5/1977 | Jepson et al. |
| 4,193,601 A | 3/1980 | Reid, Jr. et al. |
| 4,213,613 A | 7/1980 | Nygren |
| 4,214,754 A | 7/1980 | Zebelean |
| D267,965 S | 2/1983 | Kobayashi |
| 4,429,879 A | 2/1984 | Schmidt |
| 4,432,549 A | 2/1984 | Zebelean |
| 4,449,707 A | 5/1984 | Hayashi et al. |
| 4,451,041 A | 5/1984 | Hayashi et al. |
| 4,451,042 A | 5/1984 | Hayashi et al. |
| 4,465,221 A | 8/1984 | Schmidt |
| 4,471,961 A | 9/1984 | Masghati et al. |
| 4,489,945 A | 12/1984 | Kobayashi |
| 4,511,145 A | 4/1985 | Schmidt |
| 4,762,324 A | 8/1988 | Anderson |
| 4,792,140 A | 12/1988 | Yamaguchi et al. |
| 4,826,172 A | 5/1989 | Antonious |
| 4,842,243 A | 6/1989 | Butler |
| 4,869,507 A * | 9/1989 | Sahm .................... 473/337 |
| 4,913,438 A | 4/1990 | Anderson |
| 4,915,385 A | 4/1990 | Anderson |
| 4,915,386 A | 4/1990 | Antonious |
| 4,919,430 A | 4/1990 | Antonious |
| 4,919,431 A | 4/1990 | Antonious |
| 4,921,252 A | 5/1990 | Antonious |
| 4,928,965 A | 5/1990 | Yamaguchi et al. |
| 4,930,781 A | 6/1990 | Allen |
| 4,932,658 A | 6/1990 | Antonious |
| 4,955,610 A | 9/1990 | Creighton et al. |
| D312,858 S | 12/1990 | Anderson et al. |
| 5,000,454 A | 3/1991 | Soda |
| 5,024,437 A | 6/1991 | Anderson |
| 5,028,049 A | 7/1991 | McKeighen |
| 5,046,733 A | 9/1991 | Antonious |
| 5,056,705 A | 10/1991 | Wakita et al. |
| 5,060,951 A | 10/1991 | Allen |
| 5,067,715 A | 11/1991 | Schmidt et al. |
| 5,090,702 A | 2/1992 | Viste |
| 5,094,383 A | 3/1992 | Anderson et al. |
| 5,106,094 A | 4/1992 | Desbiolles et al. |
| 5,141,230 A | 8/1992 | Antonious |
| 5,163,682 A | 11/1992 | Schmidt et al. |
| 5,180,166 A | 1/1993 | Schmidt et al. |
| 5,183,255 A | 2/1993 | Antonious |
| 5,213,328 A | 5/1993 | Long et al. |
| 5,221,087 A | 6/1993 | Fenton et al. |
| 5,240,252 A | 8/1993 | Schmidt et al. |
| 5,242,167 A | 9/1993 | Antonious |
| 5,255,918 A | 10/1993 | Anderson et al. |
| 5,261,663 A | 11/1993 | Anderson |
| 5,261,664 A | 11/1993 | Anderson |
| 5,271,621 A | 12/1993 | Lo |
| 5,292,129 A | 3/1994 | Long et al. |
| 5,295,689 A | 3/1994 | Lundberg |
| 5,301,945 A | 4/1994 | Schmidt et al. |
| 5,318,300 A | 6/1994 | Schmidt et al. |
| 5,328,184 A | 7/1994 | Antonious |
| 5,344,140 A | 9/1994 | Anderson |
| 5,346,218 A | 9/1994 | Wyte |
| 5,351,958 A | 10/1994 | Helmstetter |
| 5,358,249 A | 10/1994 | Mendralla |
| 5,362,047 A | 11/1994 | Shaw et al. |
| 5,362,055 A | 11/1994 | Rennie |
| 5,390,924 A | 2/1995 | Antonious |
| 5,395,113 A | 3/1995 | Antonious |
| 5,397,126 A | 3/1995 | Allen |
| 5,401,021 A | 3/1995 | Allen |
| 5,405,136 A | 4/1995 | Hardman |
| 5,405,137 A | 4/1995 | Vincent et al. |
| 5,407,202 A | 4/1995 | Igarashi |
| RE34,925 E | 5/1995 | McKeighen |
| 5,417,419 A | 5/1995 | Anderson et al. |
| 5,417,559 A | 5/1995 | Schmidt |
| 5,423,535 A | 6/1995 | Shaw et al. |
| 5,429,357 A | 7/1995 | Kobayashi |
| 5,431,396 A | 7/1995 | Shieh |
| 5,433,440 A | 7/1995 | Lin |
| 5,447,307 A | 9/1995 | Antonious |
| 5,447,309 A | 9/1995 | Vincent |
| 5,451,056 A | 9/1995 | Manning |
| 5,460,376 A | 10/1995 | Schmidt et al. |
| 5,467,983 A | 11/1995 | Chen |
| 5,470,069 A | 11/1995 | Schmidt et al. |
| 5,474,296 A | 12/1995 | Schmidt et al. |
| 5,482,279 A | 1/1996 | Antonious |
| 5,497,993 A | 3/1996 | Shan |
| 5,505,453 A | 4/1996 | Mack |
| 5,522,593 A | 6/1996 | Kobayashi et al. |
| 5,524,331 A | 6/1996 | Pond |
| 5,533,729 A | 7/1996 | Leu |
| 5,536,006 A | 7/1996 | Shieh |
| 5,547,630 A | 8/1996 | Schmidt |
| 5,549,297 A | 8/1996 | Mahaffey |
| 5,564,994 A | 10/1996 | Chang |
| 5,584,770 A | 12/1996 | Jensen |
| 5,595,552 A | 1/1997 | Wright et al. |
| 5,611,741 A | 3/1997 | Schmidt et al. |
| 5,611,742 A | 3/1997 | Kobayashi |
| D379,393 S | 5/1997 | Kubica et al. |
| 5,626,530 A | 5/1997 | Schmidt et al. |
| 5,643,104 A | 7/1997 | Antonious |
| 5,643,108 A | 7/1997 | Cheng |
| 5,643,110 A | 7/1997 | Igarashi |
| 5,649,872 A | 7/1997 | Antonious |
| 5,651,409 A | 7/1997 | Sheehan |
| 5,655,976 A | 8/1997 | Rife |
| 5,669,827 A | 9/1997 | Nagamoto |
| 5,669,829 A | 9/1997 | Lin |
| 5,674,132 A | 10/1997 | Fisher |
| D387,113 S | 12/1997 | Burrows |
| 5,695,411 A | 12/1997 | Wright et al. |
| 5,709,614 A | 1/1998 | Horiba |
| 5,709,615 A | 1/1998 | Liang |
| 5,711,722 A | 1/1998 | Miyajima et al. |
| 5,716,292 A | 2/1998 | Huang |
| 5,718,641 A | 2/1998 | Lin |
| 5,720,673 A | 2/1998 | Anderson |
| 5,743,813 A | 4/1998 | Chen et al. |
| 5,753,170 A | 5/1998 | Muang |
| 5,755,624 A | 5/1998 | Helmstetter |
| 5,762,567 A | 6/1998 | Antonious |
| 5,766,092 A | 6/1998 | Mimeur et al. |
| 5,766,094 A | 6/1998 | Mahaffey et al. |
| 5,766,095 A | 6/1998 | Antonious |
| 5,776,011 A | 7/1998 | Su et al. |
| 5,797,807 A * | 8/1998 | Moore .................... 473/345 |

| | | | | | | |
|---|---|---|---|---|---|---|
| 5,807,190 | A | 9/1998 | Krumme et al. | JP | 05237207 | 9/1993 |
| 5,827,132 | A | 10/1998 | Bamber | JP | 6007487 | 1/1994 |
| RE35,955 | E | 11/1998 | Lu | JP | 06031016 | 2/1994 |
| D401,652 | S | 11/1998 | Burrows | JP | 6114126 | 4/1994 |
| 5,830,084 | A | 11/1998 | Kosmatka | JP | 6126002 | 5/1994 |
| 5,839,975 | A | 11/1998 | Lundberg | JP | 6154367 | 6/1994 |
| 5,842,934 | A | 12/1998 | Ezaki et al. | JP | 6182005 | 7/1994 |
| 5,851,159 | A | 12/1998 | Burrows | JP | 6269518 | 9/1994 |
| 5,863,261 | A | 1/1999 | Eggiman | JP | 8168541 | 7/1996 |
| 5,873,791 | A | 2/1999 | Allen | JP | 8243194 | 9/1996 |
| 5,873,795 | A | 2/1999 | Woznyet et al. | JP | 8280853 | 10/1996 |
| D406,294 | S | 3/1999 | Burrows | JP | 8280854 | 10/1996 |
| 5,888,148 | A | 3/1999 | Allen | JP | 8294550 | 11/1996 |
| 5,890,973 | A | 4/1999 | Gamble | JP | 9028842 | 2/1997 |
| D411,272 | S | 6/1999 | Burrows | JP | 9047531 | 2/1997 |
| 5,908,357 | A | 6/1999 | Hsieh | JP | 9154985 | 6/1997 |
| 5,921,872 | A | 7/1999 | Kobayashi | JP | 9168613 | 6/1997 |
| 5,931,746 | A | 8/1999 | Soon | JP | 09192270 | 7/1997 |
| 5,935,019 | A | 8/1999 | Yamamoto | JP | 09192273 | 7/1997 |
| 5,938,541 | A | 8/1999 | Allen et al. | JP | 9239074 | 9/1997 |
| 5,941,782 | A | 8/1999 | Cook | JP | 9239075 | 9/1997 |
| 5,944,619 | A | 8/1999 | Cameron | JP | 9248353 | 9/1997 |
| 5,954,596 | A | 9/1999 | Noble et al. | JP | 2717759 | 11/1997 |
| 5,961,394 | A | 10/1999 | Minabe | JP | 9294833 | 11/1997 |
| 5,967,905 | A | 10/1999 | Nakahara et al. | JP | 9299519 | 11/1997 |
| 5,971,868 | A | 10/1999 | Kosmatka | JP | 10024126 | 1/1998 |
| 5,993,329 | A | 11/1999 | Shich | JP | 10024128 | 1/1998 |
| 6,007,432 | A | 12/1999 | Kosmatka | JP | 10085369 | 4/1998 |
| 6,027,416 | A | 2/2000 | Schmidt et al. | JP | 10118227 | 5/1998 |
| 6,248,025 | B1 | 6/2001 | Murphy | JP | 10137372 | 5/1998 |
| 6,319,150 | B1 * | 11/2001 | Werner et al. ............... 473/349 | JP | 10155943 | 6/1998 |
| 6,338,683 | B1 | 1/2002 | Kosmatka | JP | 10258142 | 9/1998 |
| 6,354,962 | B1 | 3/2002 | Galloway | JP | 10263121 | 10/1998 |
| 6,368,234 | B1 | 4/2002 | Galloway | JP | 10323410 | 12/1998 |
| 6,381,828 | B1 | 5/2002 | Boyce | JP | 10337347 | 12/1998 |
| 6,390,933 | B1 | 5/2002 | Galloway | | | |
| 6,755,627 | B2 | 6/2004 | Chang | | | |

FOREIGN PATENT DOCUMENTS

| | | |
|---|---|---|
| JP | 4020357 | 1/1992 |
| JP | 4327864 | 11/1992 |
| JP | 5212526 | 8/1993 |

OTHER PUBLICATIONS

Golf Digest, Dec., 1981, p. 58–59.

"Variable Face Thickness Technology," Calloway Golf advertisement, undated.

* cited by examiner

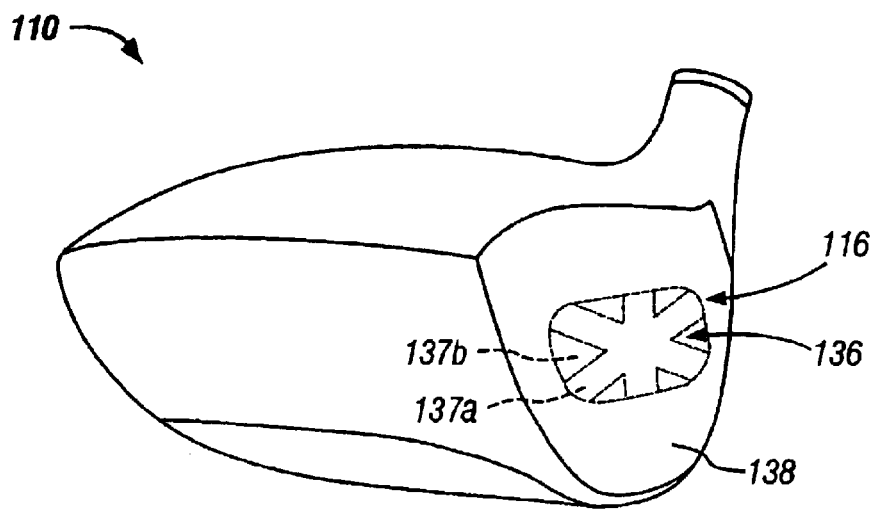
FIG. 6
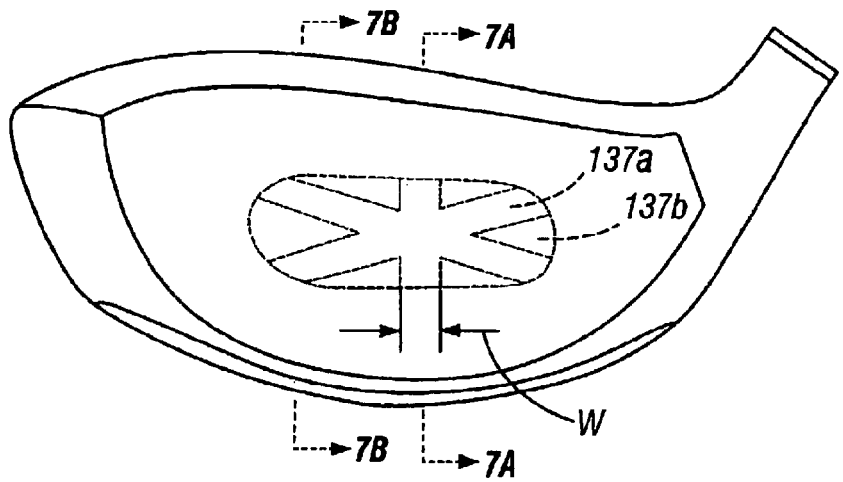
FIG. 7
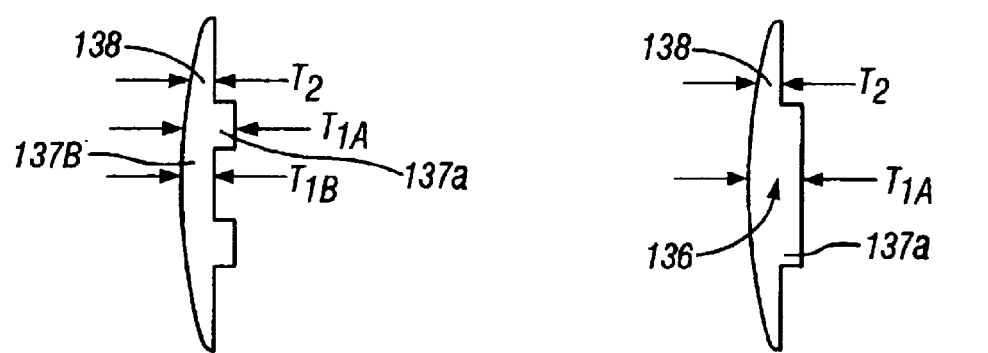
FIG. 7A     FIG. 7B

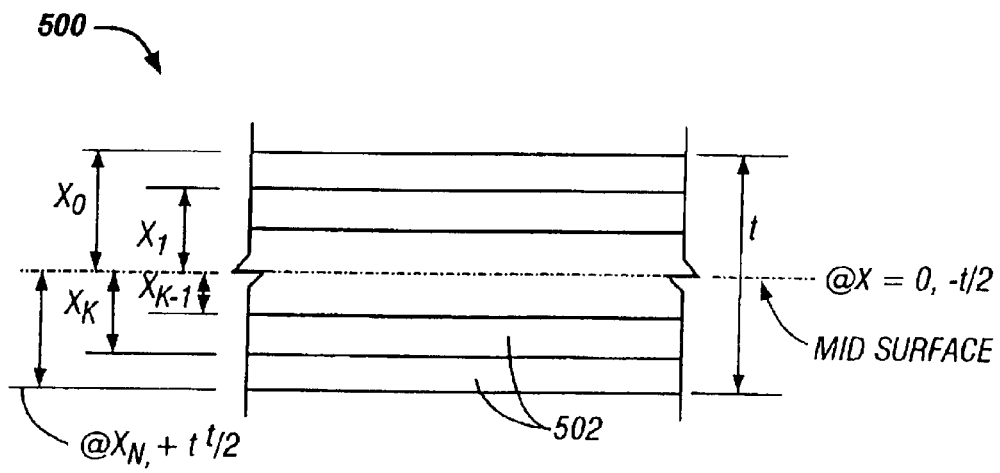
FIG. 14
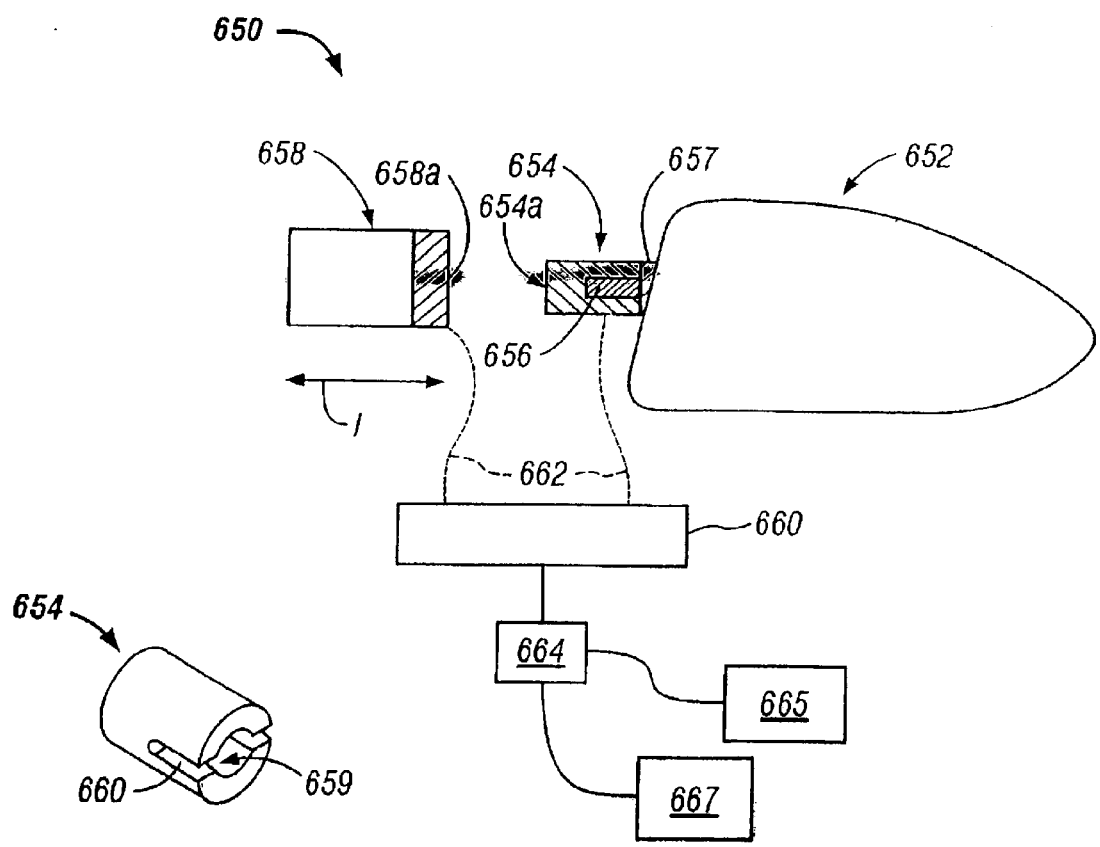
FIG. 15A    FIG. 15

GOLF CLUB HEAD WITH A HIGH COEFFICIENT OF RESTITUTION

This application is a continuation of U.S. patent application Ser. No. 09/551,771, filed Apr. 18, 2000, now U.S. Pat. No. 6,605,007, which is incorporated in its entirety by reference herein.

FIELD OF THE INVENTION

The invention is an improved golf club head. More particularly, the invention is a golf club head with an improved striking face having discrete zones with varying flexural stiffness, improved accuracy, and a high coefficient of restitution.

BACKGROUND OF THE INVENTION

The complexities of golf club design are well-known. The choice of specifications for each component of the club (i.e., the club head, shaft, hosel, grip, and subcomponents thereof) directly impacts the performance of the club. Thus, by varying the design specifications, a golf club can be tailored to have desirable performance characteristics.

The design of club heads has long been studied. Among the more prominent considerations in club head design are loft, lie, face angle, horizontal face bulge, vertical face roll, face progression, face size, sole curvature, center of gravity, material selection, and overall head weight. While this basic set of criteria is generally the focus of golf club engineering, several other design aspects must also be addressed. The interior design of the club head may be tailored to achieve particular characteristics, such as by including hosel or shaft attachment means, perimeter weighting on the face or body of the club head, and fillers within hollow club heads.

The designs for golf club heads must also be strong enough to withstand the impact forces that occur during collision between the head and the ball. The loading that occurs during this transient event can cause an acceleration to the golf ball that is four orders of magnitude greater than that of gravity. Thus, the club face and body should be designed to resist permanent deformation or catastrophic failure, by material yield or fracture.

It is not unusual for club heads of prior art hollow metal woods, produced from titanium, to have a uniform face thickness exceeding 0.15 inches. This thickness has been required to ensure structural integrity of the club head during impact.

Players generally seek a wood and golf ball combination that delivers maximum distance and landing accuracy. The distance a ball travels after impact is dictated by the magnitude and direction of the ball's translational velocity and the magnitude and direction of the ball's rotational velocity or spin. Environmental conditions, including atmospheric pressure, humidity, temperature, and wind speed further influence ball flight. However, these environmental effects are beyond the control of the golf equipment manufacturer. Golf ball landing accuracy is driven by a number of factors as well. Some of these can be attributed to club head design. Primarily, of concern here are center of gravity and club face flexibility.

Golf ball distance is a function of the total kinetic energy imparted to the ball during impact with the club head, neglecting environmental effects. During impact, kinetic energy is transferred from the club and stored as elastic strain energy in the club head and the ball. After impact, the stored elastic energy is transformed back into kinetic energy in the form of translational and rotational velocity of the ball as well as the club. Since the collision is not perfectly elastic, a portion of energy is dissipated in club head vibration and viscoelastic relaxation of the ball. Viscoelastic relaxation is a material property of the polymeric materials used in all manufactured golf balls.

The United States Golf Association (USGA), the governing body for the rules of golf in the United States, has specifications for the performance of golf balls. These performance specifications dictate the size and weight of a golf ball that conforms to the USGA. Furthermore, there are USGA rules which limit the golf ball velocity after a prescribed impact to 250 feet per second ±5%. To achieve greater golf ball distance, ball velocity after impact must be maximized while remaining within these guidelines. Viscoelastic relaxation of the ball is a parasitic energy source, which is dependent upon the rate of deformation. To minimize this effect, the rate of deformation must reduced. This may be accomplished by allowing more club face deformation during impact. Since metallic deformation maybe purely elastic, the strain energy stored in the club face is returned to the ball after impact thereby increasing the ball's outbound velocity after impact.

A variety of techniques may be utilized to vary the allowable deformation of the club face. For example, uniform face thinning, thinned faces with ribbed stiffeners and a varied thickness on the face profile are three possibilities. Any design must have sufficient structural integrity to withstand impact without permanent deformation of the club face.

In general, prior art club heads exhibit large variations in the coefficient of restitution (COR) magnitude with impact location on the face of the club. Furthermore, accuracy of those prior art clubs are highly dependent on this impact location.

Thus, there is a need for a golf club with a face that maximizes golf ball distance while maintaining accuracy due to a reduced sensitivity to face impact location. Furthermore, it would be desirable for the improved club design to minimize the dissipation of spurious energy modes of structural vibration of the club to further maximize efficient energy transfer after impact.

SUMMARY OF THE INVENTION

The present invention relates to a golf club head adapted for attachment to a shaft. The head includes a face and a body. The face is configured and dimensioned so that it includes a central portion and an adjacent surrounding intermediate portion. The central portion is rigid and the intermediate portion is relatively flexible so that upon ball impact, the intermediate portion of the face deforms to provide high ball velocity, while the central portion is substantially undeformed so that the ball flies on-target. Thus, upon ball impact the deformation of the intermediate portion allows the central region to move into and out of the club head as a unit. As a result, the head exhibits a coefficient of restitution greater than 0.81.

The above is accomplished by providing the central portion with a first flexural stiffness and the intermediate portion with a second flexural stiffness. Flexural stiffness is defined as the portion's Elastic modulus (E) times the portion's thickness (t) cubed or $Et^3$. The first flexural stiffness is substantially different from the second flexural stiffness. As a result, upon ball impact, the intermediate portion exhibits substantial deformation so that the central portion moves into the club head, and the central portion exhibits minimal deformation.

In one embodiment, the first flexural stiffness is at least three times the second flexural stiffness. In other embodiments, the first flexural stiffness is six to twelve times the second flexural stiffness.

More preferably, the first flexural stiffness is greater than 25,000 lb-in. Most preferably, the first flexural stiffness is greater than 55,000 lb-in. Preferably, the second flexural stiffness is less than 16,000 lb-in. More preferably, the second flexural stiffness is less than 10,000 lb-in.

Since the flexural stiffness is a function of material and thickness, the following techniques can be used to achieve the substantial difference between the first and second flexural stiffnesses: 1) different materials can be used for each portion, 2) different thicknesses can be used for each portion, or 3) different materials and thicknesses can be used for each portion. For example, in one embodiment, the thickness of the central portion is greater than the thickness of the intermediate portion and the material for both portions is titanium.

The golf club head further includes a perimeter portion disposed between the intermediate portion and the body. In one embodiment, the perimeter portion has a third flexural stiffness that is at least two times greater than the second flexural stiffness. The area of the perimeter portion preferably comprises less than 30% of the total area of the club head face.

In an alternative embodiment, a golf club head includes a shell that defines an inner cavity and a face. The face defines a face area and includes a first portion in the center and a second portion adjacent thereto. The first portion has a first thickness and defines a first area. The second portion has a second thickness. The first area is between about 15% and about 60% of the total face area, and the first thickness is greater than the second thickness. More preferably, the first area is between about 20% and 50% of the face area.

In the club heads discussed above, the first, second, and third portions can have various shapes, such as the shape of the face or an elliptical shape. Furthermore, the club head inner cavities can have a volume greater than about 250 cubic centimeters, and more preferably a volume greater than about 275 cubic centimeters. It is recommended that the face of the club head have a loft of greater than about 13°.

In addition, the central, intermediate, and perimeter portions can each have variable thicknesses. One feature of the present invention is specifically locating the center of gravity of the club head with respect to a first, second and third axes. The shell further includes a top portion and a spaced sole plate, a heel portion and a spaced toe portion, and a rear spaced from the face. The first axis extends between the top portion and the sole plate. The second axis extends between the heel portion and the toe portion. The third axis extends between the face and the rear portion. The axes meet at the geometric center of the face and the center of gravity is defined with respect to the geometric center of the face. The center of gravity is preferably toward the middle of the second axis and on the third axis at or below the first axis such that the center of gravity is behind the center of the face or lower. Preferably, the center of gravity is on a point of the third axis within the central portion. In one embodiment, the center of gravity is spaced from the geometric center along the first axis by a first distance of at least about 0.1". More preferably, the center of gravity is spaced from the geometric center along the first axis toward the sole plate, wherein the first distance is at least about 0.15". In another embodiment, the center of gravity is spaced a second distance from the geometric center along the second axis, wherein the second distance is less than about 0.02". In addition, the center of gravity is spaced a third distance from the geometric center along the third axis toward the rear portion, wherein the third distance is less than about 1.25".

The present invention is also directed to a golf club head adapted for attachment to a shaft that comprises a face. The face includes a total face area and first primary resonant frequency, which is less than about 2900 Hz. The face further includes a central zone that includes a geometric center of the face, and an intermediate zone disposed adjacent the central zone. The central zone has a first flexural stiffness and a central zone area that is at least 15% of the total face area. The intermediate zone has a second flexural stiffness. The first flexural stiffness is at least 25,000 lb-in and greater than the second flexural stiffness.

BRIEF DESCRIPTION OF THE DRAWINGS

Preferred features of the present invention are disclosed in the accompanying drawings, wherein similar reference characters denote similar elements throughout the several views, and wherein:

FIG. 6 is a toe side, front, perspective view of a second embodiment of a golf club head of the present invention;

FIG. 7 is a front, elevational view of the golf club head of FIG. 6;

FIG. 7A is a cross-sectional view of the face of the golf club head of FIG. 7 along line 7A—7A;

FIG. 7B shows a cross-sectional view the face of the golf club head of FIG. 7 along line 7B—7B;

FIG. 14 is an enlarged, elevational view of a portion of the face of a laminated golf club head of the present invention;

FIG. 15 is a schematic representation of a testing apparatus for obtaining frequency response data from a club head;

FIG. 15A is a perspective view of an attached mass for use with the testing apparatus of FIG. 15;

DETAILED DESCRIPTION OF THE PREFERRED EMBODIMENT

Figure 5:
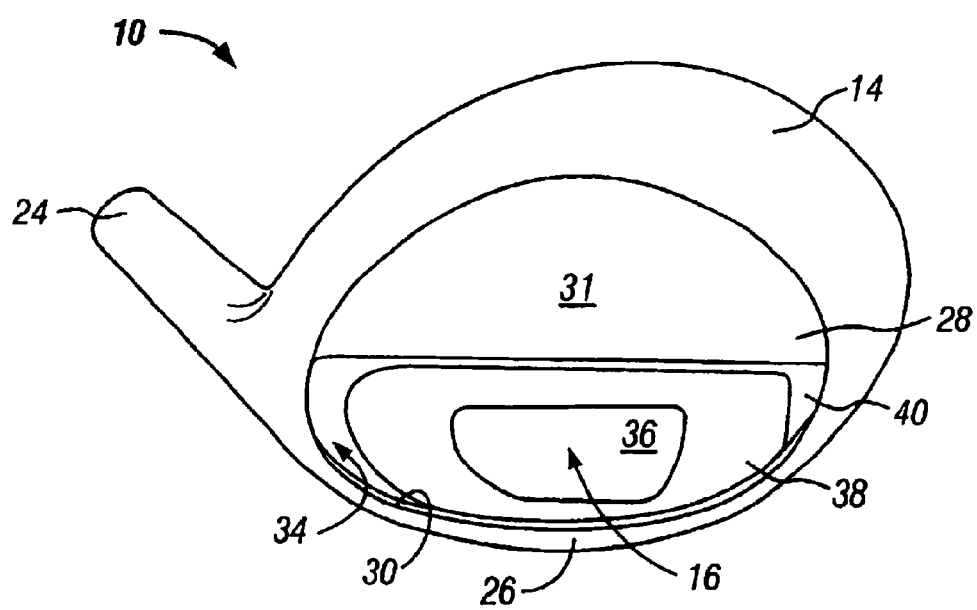
FIG. 5 is a bottom, perspective view of the golf club head of FIG. 1.

Referring to FIGS. 1–5, a first embodiment of a golf club head 10 of the present invention is shown. Club head 10 includes shell 12 with body 14, face 16, toe portion 18, heel portion 20, sole plate 22, hosel 24, bottom portion 26, crown portion 28, and rear portion 29. The sole plate 22 fits in a recess 30 (as shown in FIG. 5) in the bottom portion 26 of body 14. The shell 12 and sole plate 22 create an inner cavity 31 (as shown in FIG. 5). The face 16 has an exterior surface 32 and an interior surface 34. The exterior surface 32 may optionally have grooves 35.

A golf club shaft (not shown) is attached at hosel 24 and is disposed along a shaft axis SHA. The hosel may extend to the bottom of the club head, may terminate at a location between the top and bottom portions of the head, or the hosel can terminate flush with the top portion and extend into the cavity in the head.

Inner cavity 31 of club head 10 may be empty, or alternatively may be filled with a foam or other low specific gravity material. It is recommended that the inner cavity 31 has a volume greater than 250 cubic centimeters, and more preferably greater than 275 cubic centimeters. Preferably, the mass of the inventive club head is greater than 150 grams but less than 220 grams.

Figure 3:
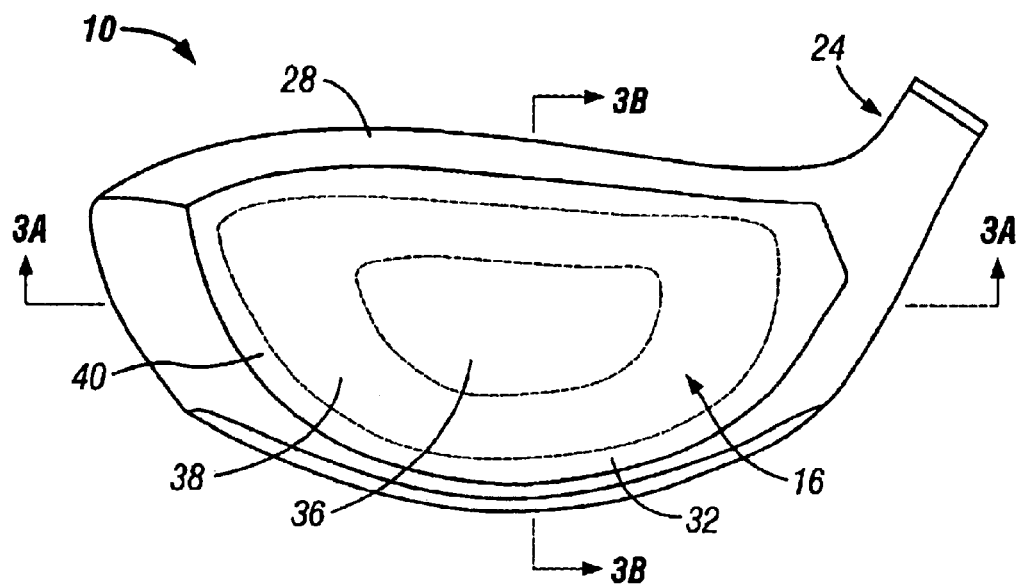
FIG. 3 is a front, elevational view of the golf club head of FIG. 1.
Figure 3A:
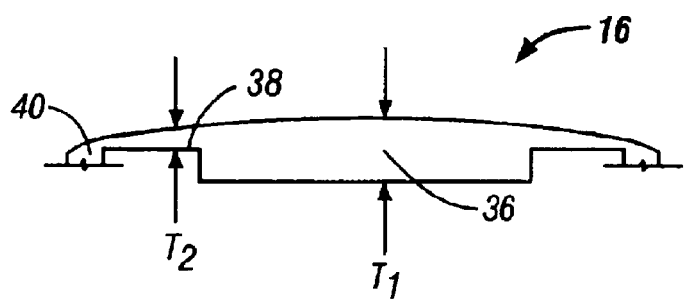
FIG. 3A is a cross-sectional view of the face of the golf club head of FIG. 3 along line 3A—3A.
Figure 3B:
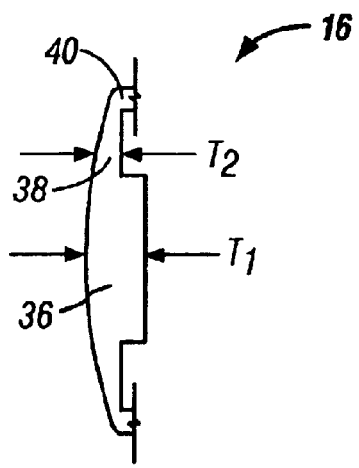
FIG. 3B shows a cross-sectional view the face of the golf club head of FIG. 3 along line 3B—3B.
Figure 4:
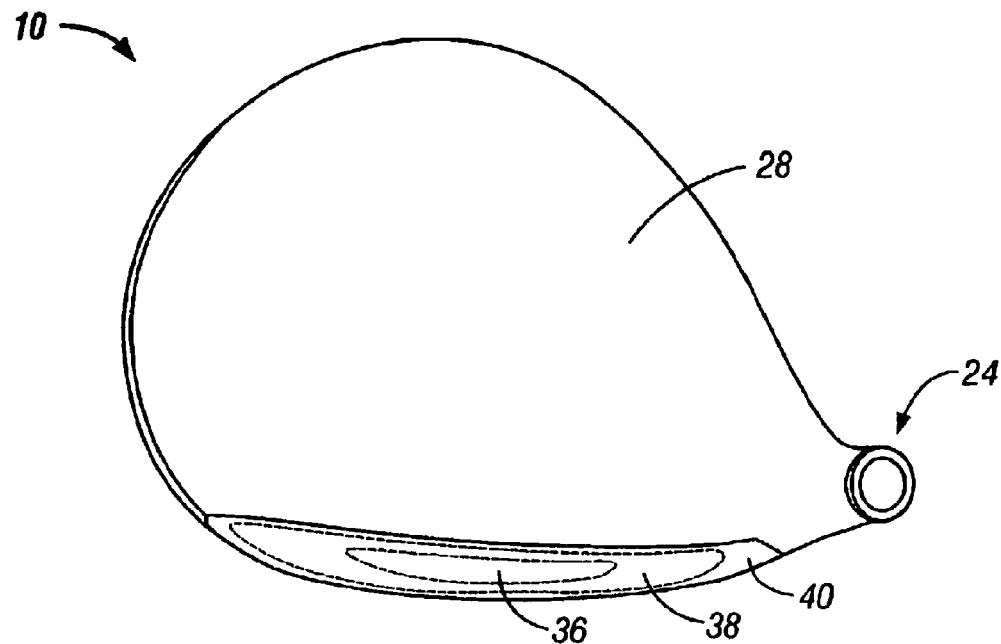
FIG. 4 is a top view of the golf club head of FIG. 1.

Referring to FIGS. 3–3B, the face 16 includes a central zone or portion 36, an intermediate zone or surrounding portion 38 adjacent the central zone 36, and a perimeter zone or outer portion 40. The central zone 36 is surrounded by the intermediate zone 38 and the perimeter zone 40 surrounds the intermediate zone 38. The perimeter zone 40 is the zone between the intermediate zone 38 and crown portion 28. In the following specification and claims, the central zone 36 is a contiguous zone centrally located on the face 16 and containing a geometric center GC of the face.

The zone 36, 38 and 40 have a shape that is the similar to the shape of the face 16 only with a smaller area, as discussed in detail below. The central zone 36 has a first thickness $t_1$. The intermediate zone 38 has a second thickness $t_2$. The first thickness $t_1$ is greater than the second thickness $t_2$. Typically, when the club head is cast, the perimeter zone 40 will be thicker than the intermediate zone 38. However, the present invention is not limited to this configuration. Preferably, the first thickness $t_1$ is equal to about one and a half (1.5) times the thickness $t_2$ to about four (4) times the thickness $t_2$ of the intermediate zone 38 or surrounding portion.

The thickness relationships between the zones 36, 38, and 40 are provided so that a predetermined relationship exists between flexural stiffness exhibited by each of the zones. Flexural stiffness (FS) is defined by the following formula:

$$FS = E * t^3$$

where,

E = the Elastic Modulus of the material; and t = the thickness of the material.

The central zone 36 has a first flexural stiffness $FS_1$. The intermediate zone 38 has a second flexural stiffness $FS_2$. The perimeter zone 40 has a third flexural stiffness $FS_3$. The predetermined relationship between the portions is that the first flexural stiffness $FS_1$ is substantially greater than the second flexural stiffness $FS_2$, and optionally the third flexural stiffness $FS_3$ is substantially greater than the second flexural stiffness $FS_2$. Preferably, the first flexural stiffness $FS_1$ is at least three times greater than the second flexural stiffness $FS_2$. As a ratio the following relationship must be satisfied $$\frac{FS_1}{FS_2} \geq 3.$$

This expression means the ratio of the central zone flexural stiffness $FS_1$ over the intermediate zone flexural stiffness $FS_2$ is equal to or greater than 3.0. When the above ratio of flexural stiffnesses is less than three the central zone sustains excessive deformation during impact and accuracy of the club is diminished. More preferably, the first flexural stiffness $FS_1$ is at least six to twelve times greater than the second flexural stiffness $FS_2$. Most preferably, the first flexural stiffness $FS_1$ is about eight times greater than the second flexural stiffness $FS_2$.

Preferably, the third flexural stiffness $FS_3$ is at least two times greater than the second flexural stiffness $FS_2$. Thus, the following relationship must be satisfied:

$$\frac{FS_3}{FS_2} \geq 2.$$

In club head 10 (as shown in FIG. 3), the above flexural stiffness relationships are achieved by selecting a certain material with a particular Elastic modulus and varying the thickness of the zones. In another embodiment, the flexural stiffness relationships can be achieved by varying the materials of the zones with respect to one another so that the zones have different Elastic moduli and the thickness is changed accordingly. Thus, the thickness of the portions can be the same or different depending on the Elastic modulus of the material of each portion. It is also possible to obtain the required flexural stiffness ratio through the use of structural ribs, reinforcing plates, and thickness parameters.

Quantitatively, it is preferred that the first flexural stiffness $FS_1$ is greater than 20,000 lb-in. When the first flexural stiffness is less than 20,000 lb-in excessive deformation of the central region can occur during impact and accuracy is diminished. More preferably, the first flexural stiffness $FS_1$ is greater than 55,000 lb-in. Preferably, the second flexural stiffness $FS_2$ is less than 16,000 lb-in. When the second flexural stiffness is greater than 18,000 lb-in the COR the resultant ball velocity is reduced. More preferably, the second flexural stiffness $FS_2$ is less than 10,000 lb-in and, most preferably, less than 7,000 lb-in.

Referring to FIG. 3, it is recommended that central portion 36 has a first area that is between about 15% and about 60% of the exterior surface area 32 or face area. The percentage of face area is computed by dividing the area of each zone 36, 38, or 40 by the total face area of exterior surface 32. It should be noted that the total face area of the exterior surface 32 is equivalent to the sum of areas of the zones 36, 38, and 40. In a preferred embodiment, the central zone first area is greater than about 15% and less than about 60% of the total face area. When the central zone 36 is less than 15% of the total face area, then accuracy can be diminished. When central portion 36 is greater than 60% of the face area 32, then COR can be diminished.

Referring again to FIG. 1, the club head 10 is further formed so that a center of gravity of the club head has a predetermined relationship with respect to a Cartesian Coordinate System with a center located on the exterior surface and coincident with the geometric center GC of the face 16. The face includes a vertical centerline CL and a horizontal centerline HCl perpendicular thereto. The geometric face center GC is at the intersection of these centerlines CL and HCl. Preferably, the geometric center of the central zone 36 is coincident with the club face geometric center GC.

Figure 2:
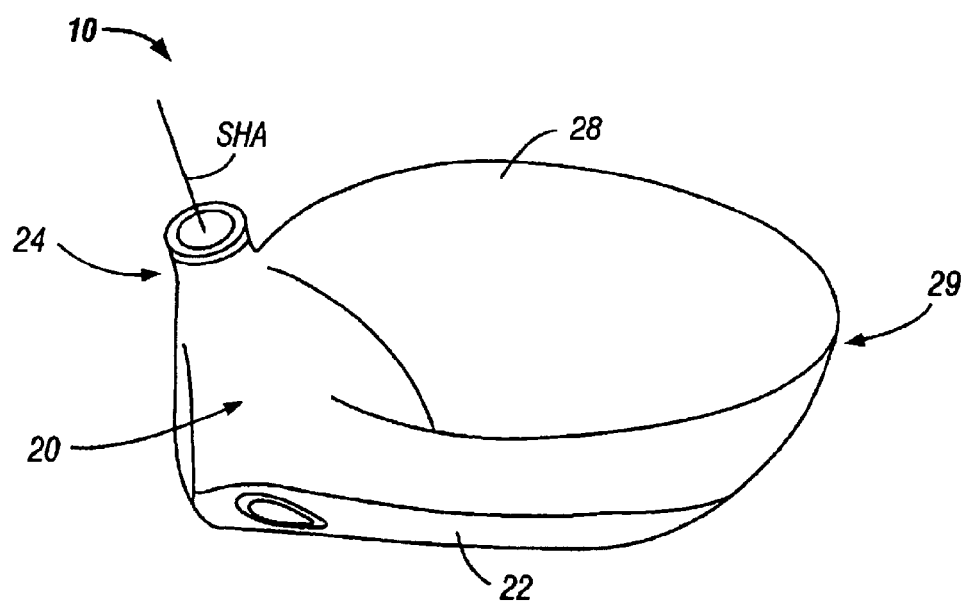
FIG. 2 is a heel side, rear, perspective view of the golf club head of FIG. 1.

The Cartesian Coordinate System is defined when the club head is resting on a flat surface (i.e., at its natural loft) and includes three axes. A vertical or Z-axis is coincident with a gravity vector, g, that acts on the club head. A first direction of the club head extends along the verticle or Z-axis between the crown portion 28 and the sole plate 22. The positive Z-direction is toward the crown portion 28. A horizontal or X-axis is perpendicular to the z-axis. A second direction of the club head extends along the X-axis between heel portion 20 (as shown in FIG. 2) and toe portion 18. The positive X-direction is toward the toe portion 20. A Y-axis is perpendicular to both the Z-axis and the X-axis. A third direction of the club head extends along the Y-axis between the face 16 and the rear portion 29. The positive Y-direction is toward the rear portion 29.

Figure 1:
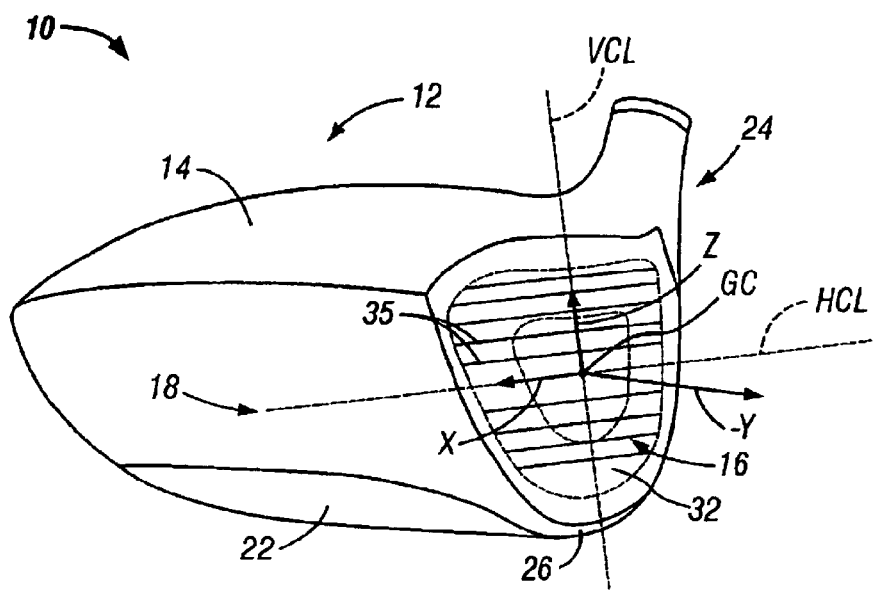
FIG. 1 is a toe side, front, perspective view of a first embodiment of a golf club head of the present invention.

Referring to FIG. 1, the location of the center of gravity is defined by coordinates for the center of gravity $CG_z$, $CG_y$, and $CG_x$ with respect to the Z, X, and Y axes, respectively. In the vertical direction along the Z-axis, the center of gravity coordinate is designated $CG_z$ and is spaced a first distance D1 from the geometric face center G along the Z-axis. The first distance D1 is at least about −0.1 inches, and more preferably the first distance D1 is at least about −0.15 inches so that the center of gravity in the vertical direction is below the geometric center GC.

In the horizontal direction along the X-axis, the center of gravity coordinate is designated $CG_x$, and is spaced a second distance D2 from the geometric face center GC. The second distance D2 is less than about 0.02 inches and greater than −0.02 inches so that the center of gravity in the horizontal direction is spaced from the center GG by no further than the magnitude of distance D2.

Referring to FIG. 1, along the Y-axis, the center of gravity coordinate is designated $CG_y$, and is spaced a third distance D3 from the geometric face center GC preferably toward the rear portion 29. The center of gravity $CG_Y$ in the third direction is spaced from the center GC toward the heel portion 29 by no further than the magnitude of the third distance D3. The third distance D3 is preferably equal to or less than about 1.25 inches and, more preferably, less than about 1 inch.

EXAMPLES

These and other aspects of the present invention may be more fully understood with reference to the following non-limiting examples, which are merely illustrative of embodiments of the present invention golf club head, and are not to be construed as limiting the invention, the scope of which is defined by the appended claims.

TABLE 1

FLEXURAL STIFFNESS INFORMATION

| Parameter | Comparative Example 1 | Comparative Example 2 | Comparative Example 3 | Inventive Example |
|---|---|---|---|---|
| Thickness of Center Zone (inches) | 0.115 | 0.130 | 0.095 | 0.150 |
| Thickness of First Intermediate Zone (inches) | 0.115 | 0.100 | 0.098 | 0.075 |
| Thickness of Second Intermediate Zone (inches) | 0.115 | 0.080 | 0.100 | 0.75 |
| Thickness of Perimeter Portion (inches) | 0.115 | 0.150 | 0.120 | 0.120 |
| E of All Portions (psi) | 1.65E+0.7 | 1.65E+0.7 | 1.65E+0.7 | 1.65E+0.7 |
| FS of Center Portion (lb-in) | 25094 | 36251 | 14147 | 55688 |
| FS of First Intermediate zone (lb-in) | 25094 | 16500 | 15530 | 6961 |
| FS of Second Intermediate Zone (lb-in) | 25094 | 8448 | 16500 | 6961 |
| FS of Perimeter Zone (lb-in) | 25094 | 55688 | 28512 | 28512 |
| $FS_1/FS_2$ | 1.0 | 2.2 | 0.9 | 8.0 |
| $FS_3/FS_2$ | 1.0 | 3.4 | 1.8 | 4.1 |

Comparative Examples 1–3 are club heads configured and dimensioned as indicated above with materials so that the zones have certain values. As a result, the ratio of the central zone flexural stiffness and adjacent intermediate zone flexural stiffness for the Comparative Examples are 1.0, 2.2, and 0.9. These ratios do not satisfy the relationship that the central zone flexural stiffness is at least three times the adjacent intermediate zone flexural stiffness. On the other hand, the Inventive Example is configured and dimensioned of a material so that the ratio of central zone flexural stiffness to the adjacent intermediate portion flexural stiffness is about 8. In the examples above, the intermediate zone is defined by a first intermediate zone adjacent the central zone and a second intermediate zone adjacent the first intermediate zone. The perimeter zone is adjacent the intermediate zone(s).

Comparative Examples 1 and 3 have a ratio of perimeter zone flexural stiffness $FS_3$ to adjacent intermediate zone flexural stiffness $FS_2$ of 1.0 and 1.8. These ratios do not satisfy the relationship that perimeter zone flexural stiffness is at least twice the intermediate zone flexural stiffness. Comparative Example 2 and the Inventive Example satisfy such a ratio with values of about 3.4 and 4.1, respectively.

TABLE 2

CENTER OF GRAVITY INFORMATION

| Parameter | Comparative Example 1 | Comparative Example 2 | Comparative Example 3 | Inventive Example |
|---|---|---|---|---|
| $CG_z$ Location (inches)[1] | 0.074 | 0.074 | 0.074 | −0.120 |

TABLE 2-continued

CENTER OF GRAVITY INFORMATION

| Parameter | Comparative Example 1 | Comparative Example 2 | Comparative Example 3 | Inventive Example |
|---|---|---|---|---|
| $CG_x$ Location (inches)$^2$ | 0.133 | 0.137 | 0.137 | −0.001 |
| $CG_y$ Location (inches)$^3$ | 1.159 | 1.159 | 1.182 | 0.991 |

$^1$Positive$_z$ is above the GC
$^2$Positive$_x$ is toward the toe from GC
$^3$Positive$_y$ is toward the back from the GC The center of gravity for the Inventive Example club head was achieved by the configuration and dimensions of the club head in additional to adding a weight of 31.5 grams to the sole plate. Other known methods of weight manipulation can be used to achieve the inventive center of gravity location as set forth above.

Thus, referring to FIG. 1, in the club head example of the present invention the center of gravity is preferably located along the Z-axis at least 0.10 inches below the geometric face center GC, along the X-axis within 0.01 inches from the geometric face center GC, and along the y-axis within 1.25 inches from the geometric face center GC. The Parameter column of Table 2 describes for each center of gravity location or coordinate the distance that the center of gravity is spaced from the face geometric center GC with respect to a Cartesian Coordinate System along particular axes. The centers of gravity for Comparative Examples 1–3 are not located properly with respect to the inventive requirements along the Z- and X-axes. The center of gravity for the Inventive Example is located properly with respect to the inventive requirements in the Z, X, and Y axes.

TABLE 3

TEST RESULTS

| Parameter | Comparative Example 1 | Comparative Example 2 | Comparative Example 3 | Inventive Example |
|---|---|---|---|---|
| Maximum COR | 0.807 | 0.808 | 0.829 | 0.830 |
| Average COR | 0.765 | 0.766 | 0.783 | 0.789 |
| Maximum Total Distance (yards) | 290 | 286 | 291 | 298 |
| Landing Area (yards$^2$) | 950 | 255 | 1000 | 341 |

The test results enumerated in Table 3 were generated using computational techniques, which included finite element analysis models. When computer modeling the exemplary club heads, the following assumptions were made: club head loft of 8.5; club head mass of 201 grams; and club head material is 6AL-4V titanium alloy. The golf ball used was a two-piece solid ball. Finite element models were used to predict ball launch conditions and a trajectory model was used to predict distance and landing area. The impact condition for the swing used in the total distance and landing area predictions or tests had a club head velocity of 109.1 mph and an attack angle of +2 degrees, the club was oriented such that the vertical plane of the face was at an angle of 8.5 degrees relative to the velocity vector. The impact condition used for club coefficient of restitution (COR) tests was consistent with the USGA Rules for Golf, specifically, Rule 4-1e Appendix II Revision 2 dated Feb. 8, 1999. The impact conditions prescribed by Rule 4-1e include firing a ball at a stationary club head with a ball velocity of 160 feet per second. Rule 4-1e also prescribes that the velocity vector of the ball is nearly perpendicular to the plane of the club face.

COR or coefficient of restitution is one way of measuring ball resiliency. The coefficient of restitution (COR) is the ratio of the velocity of separation to the velocity of approach. In this model, therefore, COR was determined using the following formula:

$$(v_{club\text{-}post} - v_{ball\text{-}post})/(v_{ball\text{-}pre} - v_{club\text{-}pre});$$

where, $v_{club\text{-}post}$ represents the velocity of the club after impact;
$v_{ball\text{-}post}$ represents the velocity of the ball after impact;
$v_{club\text{-}pre}$ represents the velocity of the club before impact (a value of zero for USGA COR conditions); and
$v_{ball\text{-}post}$ represents the velocity of the ball before impact.

The COR, in general, depends on the shape and material properties of the colliding bodies. A perfectly elastic impact has a COR of one (1), indicating that no energy is lost, while a perfectly inelastic or plastic impact has a COR of zero, indicating that the colliding bodies did not separate after impact resulting in a maximum loss of energy. Consequently, high COR values are indicative of greater ball velocity and travel and total distance. Club heads with thinner faces also have higher COR values, as exhibited by Comparative Example 3 as compared to the Comparative Club 1. However, unexpectedly the Inventive Example has the highest COR. For the inventive club head, preferably the COR is greater than about 0.81, and more preferably greater than about 0.83.

It is expected that as the COR increases the ball flight distance will increase and the maximum total distance will increase. The Inventive Example with the highest COR also has the highest maximum total distance.

It as also expected that as the COR increases the shot accuracy will decrease. However, the Inventive Example with the highest COR has the greatest accuracy as illustrated by the data for Landing Area. The Landing Area is an area encompassing the position of nine balls, which impact the club face at various locations. The nine impact locations were equally spaced within a rectangular region 1 inch wide and 0.5 inches high, centered on the club face. The club head of the Inventive Example has a very small Landing Area of 341 square yards. The Comparative Example 3, which is the only Comparative Example with a sufficient COR of at least 0.81, has a Landing Area of 1000 square yards which is significantly greater than the Landing Area for the Inventive Club. The smaller the landing area, the greater the accuracy of the club.

Several alternative embodiments of the invention are possible. The features of the invention include flexural stiffness for distinct zones or portions of the club face as well as the ratio of flexural stiffness between portions. A wide variety of rib configurations and material alternatives may be used to attain the requisite flexural stiffness and flexural stiffness ratio of the face portions.

In FIGS. 3–3B, a preferred embodiment of the club 10 is shown. The club 10 has a face 16 with the following construction. The central zone 36 has a thickness, $t_1$, of about 0.150 inches, the intermediate zone 38 has thickness, $t_2$, of about 0.075 inches, and the perimeter zone 40 has thickness, $t_3$, of about 0.120 inches. Furthermore, the central zone 36 comprises about 20% of the total face surface area and the perimeter zone 40 is less than about 20% of the total face surface area. Each of the three zones 36, 38, and 40 have uniform thickness and are constructed from a single homogeneous material, preferably a titanium alloy, with a Young's Modulus (Et) of approximately $16.5 \times 10^6$ lbs/in$^2$.

Referring to FIGS. 3–3B, the flexural stiffness, FSz, can also be defined by the following relationship:

$$FSz = \sum_{i=1}^{n} \frac{A_i}{\sum_{j=1}^{n} A_j} E_i t_i^3$$

where;

$A_i$ is defined as the area of a constituent within a zone.

$E_i$ is the Young's Modulus in pounds per square inch of a constituent within a zone $t_i$ is the thickness or average thickness in inches of a constituent within a zone n is the number of constituents within a zone.

Using this expression, the flexural stiffness can be calculated for the central and abutting zones and a ratio, defined as the flexural stiffness ratio, can be computed. The flexural stiffness ratio for the preferred embodiment golf club head 10 is calculated as, $$FS_C = E_C t_C^3 = (16.5 \times 10^6 16/\text{in}^2)(0.15 \text{ in})^3 = 55{,}688 \text{ in} \cdot \text{lb}$$

$$FS_I = E_I t_I^3 = (16.5 \times 10^6 16/\text{in}^2)(0.075 \text{ in})^3 = 6981 \text{ in} \cdot \text{lb}$$

$$\frac{FS_C}{FS_I} = 8$$

In FIG. 6, an alternate embodiment of the club head 110 is shown to illustrate an alternate construction of face 116 that results in a similar flexural stiffness ratio of the central to the abutting intermediate zone as the embodiment of FIG. 3. In the club head 110, the face 116 has an elliptically shaped central zone 136 there about and adjacent thereto is an intermediate zone 138. The central zone 136 is about 30 percent of the total face surface area.

Referring to FIGS. 7–7B, the central zone 136 includes a ribbed support structure 137a (shown in phantom) that extends from the interior surface of the face. The ribbed structure asterisk-shaped, which is formed of a plurality of ribs or legs stiffens the central zone. The thickness of the ribbed portion 137a of the central zone $t_{1A}$ is about 0.225 inches. The width of the rib, w, is about 0.085 inches. The thickness of the remaining portion 137b between the ribs of the central zone $t_{1B}$ is about 0.09 inches. The ribbed structure 137a is defined such that it comprises about 25 percent of the surface area of the central zone. The intermediate zone 138 has a uniform thickness, $t_2$, of about 0.075 inches and extends to the boundary of the face 116 with no defined perimeter zone. The face 116 is preferably made of a homogeneous titanium alloy with a Young's Modulus (Et) of $16.5 \times 10^6$ lbs/in².

Referring to FIGS. 6–7B, the flexural stiffness ratio between the central and the abutting intermediate zone is computed.

Ellipse

Major axis $2b=2"$

Minor axis $2a=1"$

Ellipse Area $A_C = \pi b \, a$ $= \pi(1)(0.5) = 1.57 \text{ in}^2$

Rib Area WI=0.085 in

LI=4.60 in $A_r$=WI LI=0.39 in²

Non Rib Area $A_{NR} = A_c - A_r = (1.57 - 0.39) = 1.18$ in²

$$FS_C = \frac{A_r}{A_C} E_A(t_{1A})^3 + \frac{A_{NR}}{A_C} E_{NR}(t_{1B})^3$$

$$= (.25)\left(16.5 \times 10^6 \frac{16}{\text{in}^2}\right)(.225)^3 + (0.75)\left(16.5 \times 10^6 \frac{16}{\text{in}^2}\right)(.090)$$

$$= 56008 \text{ in} \cdot \text{lb}$$

$$FS_I = E_I t_2^3 = \left(16.5 \times 10^6 \frac{16}{\text{in}^2}\right)(0.075 \text{ in})^3$$

$$= 6961 \text{ in} \cdot \text{lb}$$

$$\frac{FS_C}{FS_I} = 8.05$$

It should be noted that ribs, welts, pimples, or other discrete thickness variations within a zone are handled as discrete elements within a particular zone and are computed in accordance with the governing definition for flexural stiffness previously detailed.

Figure 8:
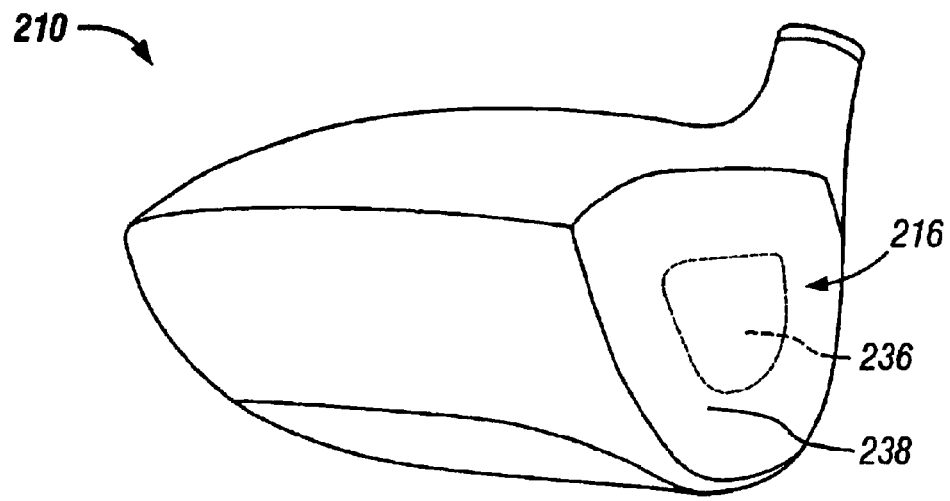
FIG. 8 is a toe side, front, perspective view of a third embodiment of a golf club head of the present invention.

In FIG. 8, an alternate embodiment of the club head 210 is shown to illustrate an alternate construction of face 216 that results in a similar flexural stiffness ratio of the central to the abutting intermediate zone as the embodiment of FIG. 3. In the club head 210, the face 216 has a central zone 236 and there about and adjacent thereto is an intermediate zone 238. The central zone 236 is about 30 percent of the total face surface area. The club head 210 does not have a defined perimeter zone.

Figure 9:
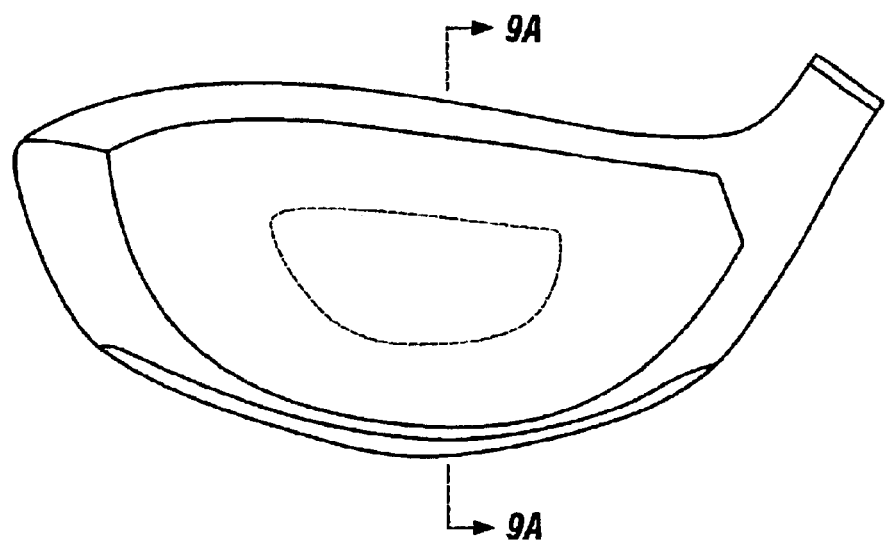
FIG. 9 is a front, elevational view of the golf club head of FIG. 8.
Figure 9A:
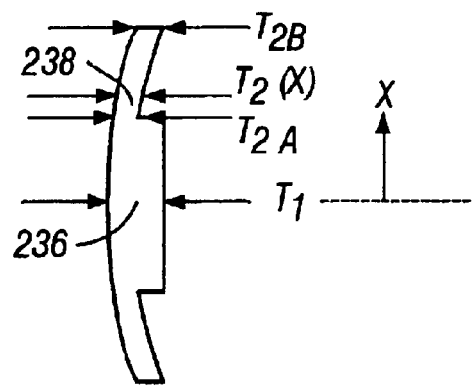
FIG. 9A is a cross-sectional view of the face of the golf club head of FIG. 9 along line 9A—9A.

Referring to FIGS. 9–9A, the central zone 236 has a uniform thickness of $t_1$ of about 0.140 inches. The intermediate zone 238 has a continuously tapering thickness from the face perimeter inward to the central zone 236. The thickness of the intermediate zone 238 is defined to change linearly.

The intermediate zone 238 has an inner thickness, $t_{2A}$, of about 0.07 inches at the boundary of the central zone 236 and the intermediate zone 238. The intermediate zone 238 has an outer thickness, $t_{2B}$, of about 0.10 inches. The outer thickness is at the face perimeter. In instances of nonuniform thickness, within the zone, and primarily in relation to a continuous taper, an average thickness may be used to compute the flexural stiffness for the zone. This approximation simplifies the calculation and is physically based on elastic shell theory.

In this embodiment, two different homogenous materials are used. The central zone 236 is preferably made from a stainless steel having a Young's Modulus (Es) of $30.0 \times 10^6$ lbs/in² and the adjacent intermediate zone 238 is made from a titanium alloy with a Young's Modulus (Et) of $16.5 \times 10^6$ lbs/in².

Referring to FIGS. 8–9A, the flexural stiffness ratio between the central and adjacent zone is computed.

$$FS_C = E_C t_1^3 = \left(30 \times 10^6 \frac{16}{\text{in}^2}\right)(0.140 \text{ in})^3$$

$$= 82320 \text{ in} \cdot \text{lb}$$

$$FS_I = E_I((t_{2A} + t_{2B})/2)^3$$

$$= 16.5 \times 10^6 \frac{16}{\text{in}^2}([0.1 + 00.7]/2)^3$$

$$= 10133 \text{ in} \cdot \text{lb}$$

$$\frac{FS_C}{FS_I} = 8.12$$

Figure 10:
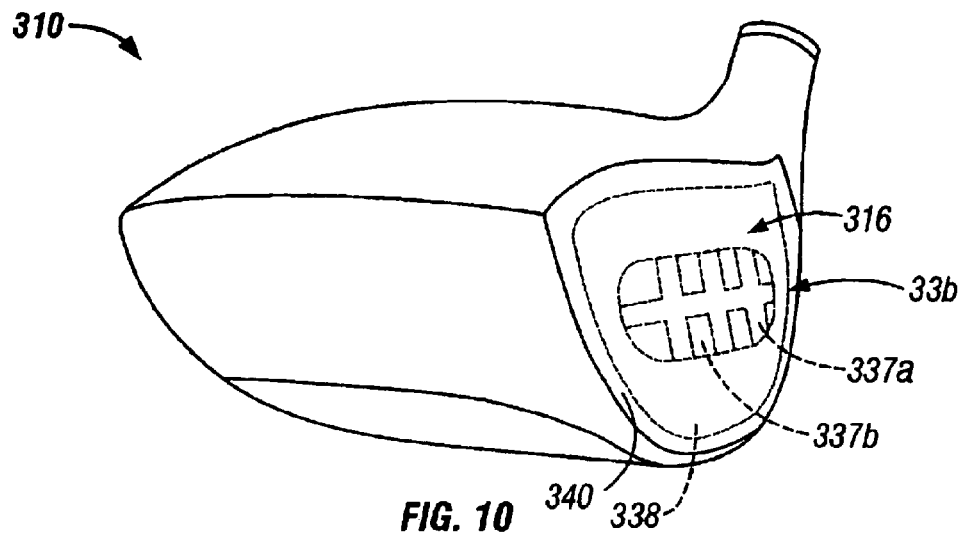
FIG. 10 is a toe side, front, perspective view of a fourth embodiment of a golf club head of the present invention.

In FIG. 10, an alternate embodiment of the club head 310 is shown to illustrate an alternate construction of face 316 that results in a similar flexural stiffness ratio of the central to the abutting intermediate zone as the embodiment of FIG. 3. In the club head 310, the face 316 has an elliptically shaped central zone 336 there about and adjacent thereto is an intermediate zone 338. The central zone 336 is formed using two materials 337a (shown in phantom) and 337b (shown in phantom).

The central zone 336 has a uniform thickness, $t_1$, of about 0.140 inches. The first material 337a is a titanium alloy with a Young's Moduli, Et, of $16.5 \times 10^6$ lbs/in². The second material 337b is stainless steel and has a Young's Moduli, Es, of $30 \times 10^6$ lbs/in². The central zone 336 is comprised of about 60 percent stainless steel, 337b.

Furthermore, the central zone 338 is elliptically shaped and comprises about 25 percent of the total face surface area. The intermediate zone 338 with the perimeter zone 340 comprises of no more than 20 percent of the total face surface area. The intermediate zone has a uniform thickness, $t_2$, of about 0.08 inches and is constructed from the same titanium alloy as the central zone 336.

Figure 11:
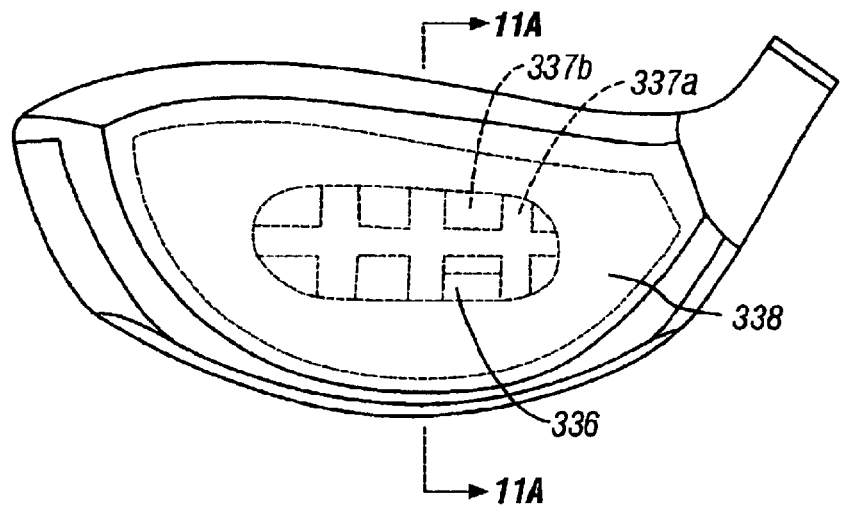
FIG. 11 is a front, elevational view of the golf club head of FIG. 10.
Figure 11A:
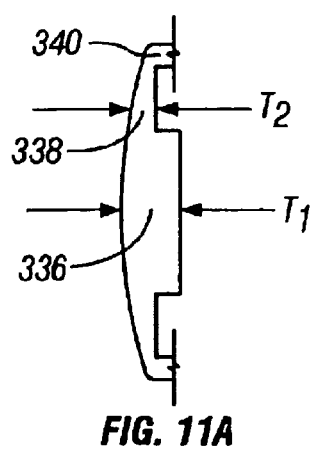
FIG. 11A is a cross-sectional view of the face of the golf club head of FIG. 11 along line 11A—11A.

Referring to FIGS. 10–11A, the flexural stiffness ratio between the central and intermediate zone 336 and 338 is computed.

Ellipse Area, $A_C$ 2b=1.8"
2a=0.9"
Ac 32 πb a
$A_C$=1.272 in²
Area Steel, $A_S$=0.763 in²
Area Non Steel, $A_{NS}=A_C-A_S$ $$FS_C = \frac{A_S}{A_C} E_S t_1^3 + \frac{A_{NS}}{A_C} E_t t_1^3$$

$$= (.6)\left(30 \times 10^6 \frac{16}{\text{in}^2}\right)(.14)^3 + (0.4)\left(16.5 \times 10^6 \frac{16}{\text{in}^2}\right)(.14)^3$$

$$= 67502 \text{ in} \cdot \text{lb}$$

$$FS_I = E_t t_2^3 = \left(16.5 \times 10^6 \frac{16}{\text{in}^2}\right)(0.08 \text{ in})^3$$

$$= 8448 \text{ in} \cdot \text{lb}$$

$$\frac{FS_C}{FS_I} = 8.0$$

The golf club head embodiments 10, 110, 210, and 310 discussed in FIGS. 1–11A demonstrate four unique face constructions which result in a similar flexural stiffness ratio, where the central zone to the adjacent zone ratio is greater than or equal to three and, more particularly, about eight. In cases where the face construction is uncertain due to manufacturing tolerances or methods or for other possible reasons, a nondestructive test method of determining the flexural stiffness ratio for a given face construction may be used.

Figure 12:
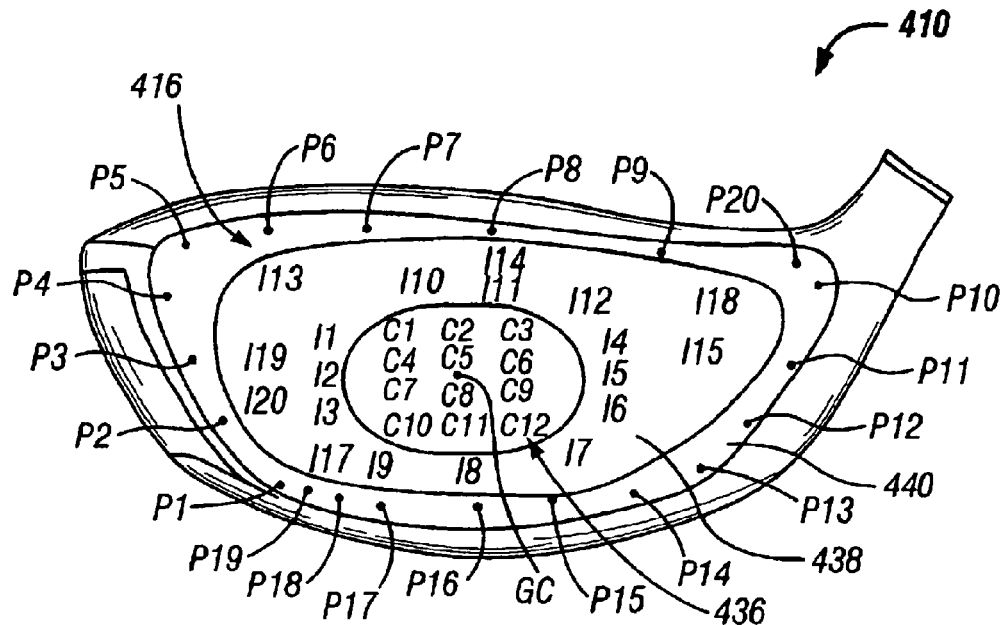
FIG. 12 is an enlarged, front view of a golf club head with ultrasonic thickness measurement locations indicated.

Referring to FIG. 12, a typical club 410 is shown with an unknown face thickness profile. Preferably, something is known regarding the construction materials of the face or has been determined experimentally through test methods known to those of ordinary skill in the art. In FIG. 7, a random distribution of points is shown on face 416. This distribution is referred to herein as a "point cloud" or predetermined point distribution. Points labeled C indicate a position in the central zone 436. Points labeled I indicate a position in the intermediate zone 438. Points labeled P indicate a position in the perimeter zone 440. The numbers following the position letters "C", "I" or "P" indicate relative face position.

Figure 13:
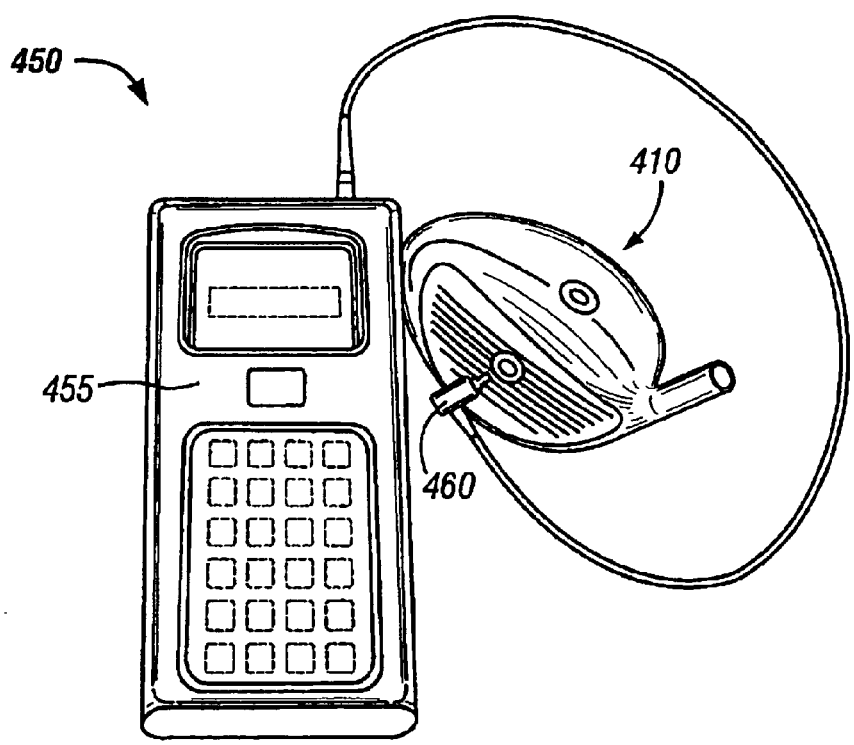
FIG. 13 is a schematic representation of the apparatus for taking an ultrasonic thickness measurement on the face of a club head.

Using the defined point cloud, an ultrasonic measurement device 450 (as shown in FIG. 13) can be used to map the face 416 thickness profile. The point cloud technique has the advantage of capturing discrete variations in face thickness such as the presence of ribs or abrupt thickness changes. One recommended ultrasonic measurement device includes a Panametrics Model 25DL ultrasonic thickness device 455 and a Panametrics model M208 probe 460. The sensor or device 455 and the probe or transducer 460 are commercially available from Panametrics, Inc. of Waltham, Mass.

Referring to FIG. 12, the face thickness data obtained from the ultrasonic measurement, along with material modulus information, is then used to define the central, intermediate and possibly perimeter zones. The central zone 436 is defined by constructing an area comprising of a specific percentage of the total face surface area and including the geometric center GC. The point cloud thickness data within the defined zone is then averaged or broken into distinct elements within the zone. If the latter is required, the area percentages for the elements within the zone are calculated. The calculation for FSz previously outlined is then carried out to determine the flexural stiffness ratio between the central and adjacent zone 436 and 438, respectively.

The following example illustrates the technique. In Table 4, random face thickness measurements are shown for titanium alloy club 410 (as shown in FIG. 12) with an unknown face thickness profile. The technique described above is used.

TABLE 4

| ULTRASONIC FACE THICKNESS DATA | | | | | |
|---|---|---|---|---|---|
| Position | Thickness | Position | Thickness | Position | Thickness |
| C1 | 0.132 | I1 | 0.102 | P1 | 0.110 |
| C2 | 0.127 | I2 | 0.103 | P2 | 0.115 |
| C3 | 0.131 | I3 | 0.098 | P3 | 0.117 |
| C4 | 0.125 | I4 | 0.096 | P4 | 0.119 |
| C5 | 0.136 | I5 | 0.088 | P5 | 0.120 |
| C6 | 0.130 | I6 | 0.089 | P6 | 0.114 |
| C7 | 0.127 | I7 | 0.089 | P7 | 0.117 |
| C8 | 0.129 | I8 | 0.094 | P8 | 0.109 |
| C9 | 0.133 | I9 | 0.097 | P9 | 0.108 |
| C10 | 0.138 | I10 | 0.099 | P10 | 0.111 |
| C11 | 0.134 | I11 | 0.100 | P11 | 0.115 |
| C12 | 0.131 | I12 | 0.103 | P12 | 0.118 |
| | | I13 | 0.106 | P13 | 0.109 |
| | | I14 | 0.102 | P14 | 0.108 |
| | | I15 | 0.105 | P15 | 0.112 |
| | | I16 | 0.101 | P16 | 0.112 |
| | | I17 | 0.100 | P17 | 0.115 |
| | | I18 | 0.103 | P18 | 0.109 |
| | | I19 | 0.107 | P19 | 0.117 |
| | | I20 | 0.106 | P20 | 0.120 |

FIG. 12 shows the measured data points and the projected central, intermediate and perimeter zones 436, 438 and 440. Based on these projected areas, the percentage of each zone can be estimated or computed more accurately by other techniques, such as face scanning. The data defines three zones, the actual central zone with an average thickness of 0.131 inches; the actual intermediate zone with an average thickness of 0.099 inches, and the perimeter zone with an average thickness of 0.114 inches. Furthermore, the area of the central zone has been estimated to be about 23 percent of the total face surface area, and the perimeter zone is estimated to comprise of about 35 percent of the total face area. Based on this information a flexural stiffness ratio can be computed as set forth below.

With regard to the calculation of face flexural stiffness and the flexural stiffness ratio. The aforementioned embodiments and point cloud example all consider faces, which possess the property of material isotropy and symmetry with regard to a mid-surface of the face structure. Material isotropy is not a necessary condition of the invention. And the invention can include club heads with anisiotropic constructions. The flexural stiffness or the flexural stiffness ratio can be used with ansiotropic constructions. These calculations would still be applicable but of a more general form, as discussed below.

The notion of symmetry with regard to a mid-surface of the face simplifies the calculations of flexural stiffness. The calculation of flexural stiffness for asymmetric shell structures with respect to the mid-surface are common in composite structures where laminate shell theory is applicable. Here the Kirkhoff shell assumptions are applicable. Referring to FIG. 14, an unsymmetric isotropic laminate 500 is shown with N lamina or layers 502. Furthermore, the laminate is described to be of thickness, t, with $x_i$ being directed distances or coordinates in accordance with FIG. 14. The positive direction is defined to be downward and the laminate points $x_i$ defining the directed distance to the bottom of the $K_{th}$ laminate layer. For example, $x_0 = -t/2$ and $x_N = +t/2$ for a laminate of thickness t made comprised of N layers.

Further complexity is added if the lamina can be constructed of multiple materials, M. In this case, the area percentage, Ai is included in the flexural stiffness calculation, as before in a separate summation over the lamina. The most general form of computing the flexural stiffness is:

$$FSz = \frac{1}{3} \sum_{j=1}^{N} Ar_j \sum_{i=1}^{M} [E(x_k^3 - x_{k-1}^3)]_i$$

Due to the geometric construction of the lamina about the mid-surface, asymmetry results, i.e., the laminate lacks material symmetry about the mid-surface of the laminate. However, this asymmetry does not change the calculated values for the flexural stiffness only the resulting forces and moments in the laminate structure under applied loads.
A conceivable example of this type of construction would be a titanium alloy face of uniform thickness and modulus $E_t$, where the central zone is backed by a steel member of with half the thickness of the titanium portion, and having modulus $E_s$. In this case, the flexural stiffness would be approximated in the following manner:

$$FSz = \frac{1}{3} \sum_{i=1} [E(x_k^3 - x_{k-1}^3)]_i$$

$$= \frac{1}{3} \{[E_S(x_o^3 - x_1^3)] + [E_t(x_1^3 - x_2^3)]\} \text{ here,}$$

$$x_0 = \frac{-t}{2}, x_1 = \frac{t}{2} - Wl, x_2$$

$$x_2 = \frac{t}{2}, \text{ substitution yielding}$$

-continued $$= \frac{1}{3}\left\{\left[E_S\left(\left(\frac{-t}{2}\right)^3 - \left(\frac{t}{2} - Wl\right)^3\right)\right] + \left[E_t\left(\left(\frac{t}{2} - Wl\right)^3 - \left(\frac{t}{2}\right)^3\right)\right]\right\}$$

Referring to FIG. 15, a testing apparatus 650 for measuring inertance is schematically illustrated. Generally, inertance is a frequency response. More specifically, inertance is a measure of the stiffness of a structure, in this instance the club face, at various frequencies of vibration. The units of inertance are acceleration units over force units. A preferred first resonant frequency for the inventive face is located where the inertance is maximized.

The test apparatus 650 includes club head 652, a rigid mass 654, an accelerometer 656, and an impact hammer 658. The mass 654 is preferably a cylindrical steel rod with a diameter of 1 inch. Referring to FIGS. 15 and 15A, the mass 654 preferably has a cylindrical cavity 659 at one end for receiving the accelerometer 656 and a slot 660 to accommodate the cable 662. The accelerometer 656 is connected to the geometric center of the face of the club head 652 with a high modulus adhesive 657, such as a cyanoacrylate based adhesive, Loctite 409, available from Loctite Corp., Newington, Conn. The mass 654 is then placed over the accelerometer 656 and also secured to the club face with cyanoacrylate adhesive. The combined mass of the mass 654 and the accelerometer 656 should equal the mass of a golf ball or 1.62 oz. The impact hammer 658 has an integral force transducer 658a and is movable toward and away from the free end 654a of the rigid mass, as indicated by the arrow I, to impact the mass 654, which is attached to the club head face at the geometric center. The impact force or excitation force is normal to the club face, and upon impact is transmitted to the face through the mass 654.

The testing apparatus 650 further includes a junction box and ICP power supply 660 and cables 662 electrically connected to the accelerometer 656 and the impact hammer transducer 658a. The junction box and ICP power supply 660 is in turn connected to a digital signal processing board 664, located within a computer 665 with signal processing software 667. The digital signal processing board 664, computer 665 and software 667 are used to condition frequency signals and calculate the frequency response functions. The accelerometer 656, transducer 658a, junction box and ICP power supply 660, cables 662, digital signal processing board 664, computer 665, and software 667 are commercially available and one of ordinary skill in the art can readily identify and obtain inertance values for golf clubs using these components. Typically, the data from 20 impacts are averaged to reduce noise and improve measurement accuracy. The following TABLE 5 lists specific model numbers for the vibration equipment shown in FIG. 13.

TABLE 5

VIBRATION EQUIPMENT

| Reference Number | Part | Model # | Supplier |
| --- | --- | --- | --- |
| 656 | Accelerometer | 352A10 | Modal Shop of Cincinnati, OH |
| 658 | Impact Hammer | 086C01 | Modal Shop |
| 662 | Cables | 002T01 | Modal Shop |
| 660 | Junction Box & ICP power | BNC 2140 | National Instruments of Dallas, TX |
| 664 | DSP Board | NI 4551 | National Instruments |

TABLE 5-continued

VIBRATION EQUIPMENT

| Reference Number | Part | Model # | Supplier |
|---|---|---|---|
| 665 | Computer | Dell Optiplex Gxi | Dell Computers of Round Rock, TX |
| 667 | Software | Virtual Bench DSA 2.5.1 | National Instruments |

Figure 16:
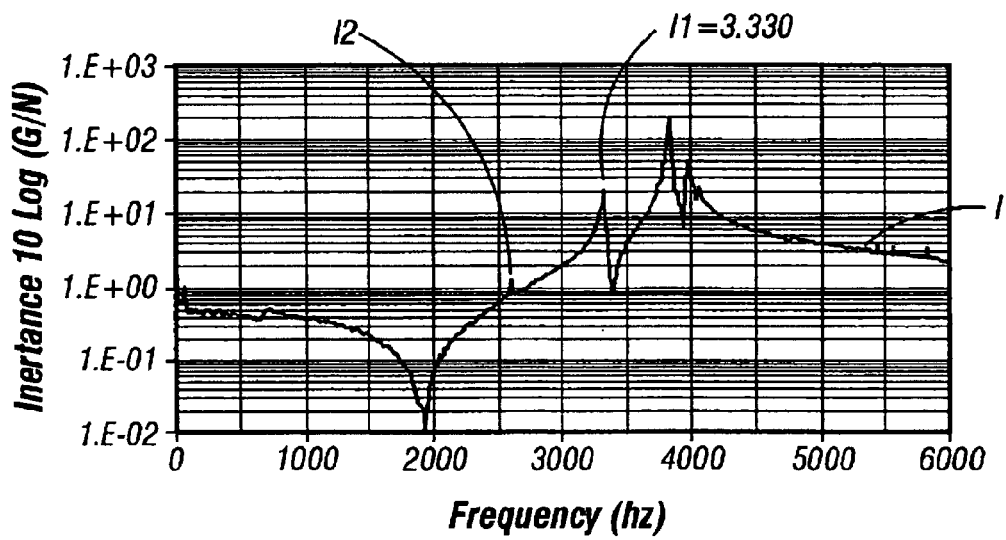
FIG. 16 is a graph of inertance versus frequency for a conventional club head.

Referring to FIG. 16, a graph of inertance versus frequency for a conventional club head is shown. The conventional club head is a Callaway Great Big Bertha War Bird with an eight degree loft. The inertance I shown is the result of testing using apparatus 650 of FIG. 15. The point I1 at a frequency of 3330 Hertz represents the first primary resonant frequency which occurs at the first primary maxima inertance for the inertance function I. A maxima which does not represent a primary resonant natural frequency of the face is also present in FIG. 16 at a frequency of 2572 Hertz, which is the point I2. These secondary maxima I2 are characterized by inertance transitions of a magnitude of less than 10 decibels. These secondary maxima may be due to crown, sole or skirt vibrations that are not acting perpendicular to the plane of the club face. Secondary maxima do not correlate with COR and ball velocity, since the vibration response is either small in magnitude or alternately not coincident with ball response. The COR for the conventional club head tested was measured in accordance with USGA, Rule 4-1e Appendix II Revision 2 dated Feb. 8, 1999 and was found to be 0.785. The preferred first primary resonant frequency of vibration is defined by the following relationship:

$$1/(2*contact\ duration) < I1 < 3/(2*contact\ duration)$$

The contact duration is the time interval during which the ball is in contact with the club face. The contact duration for a typical driver impact is about 500 microseconds. Thus, the preferred primary resonant frequency of vibration for the club head is between about 1000 and 3000 Hz. The closer the COR is to the lower limit, the higher the COR and thus the higher the rebound ball velocity. More preferably, the first primary resonant frequency is less than 2900.

Figure 17:
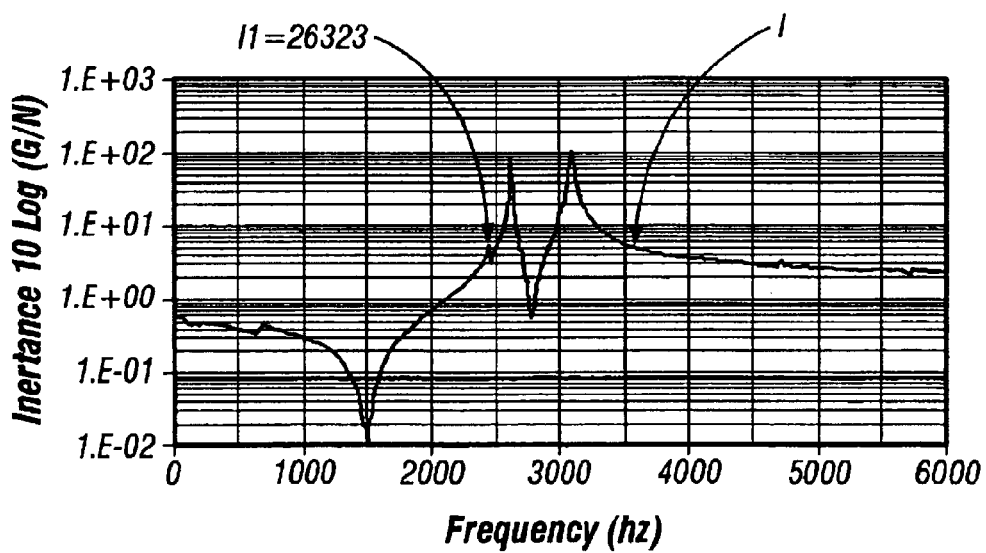
FIG. 17 is a graph of inertance versus frequency for the inventive club head.

FIG. 17 illustrates the inertance function of the invention club head. The first primary resonant frequency is at 2632 Hz, and the COR of this invention club was measured to be 0.824. The COR of the invention club is greater than the conventional club of FIG. 16, and therefore will provide greater ball rebound velocity.

Figure 18:
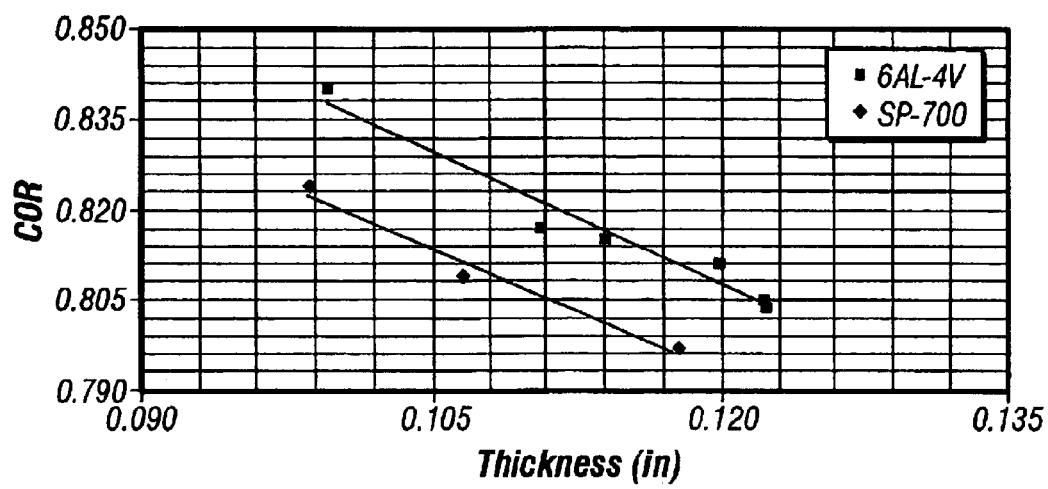
FIG. 18 is a graph of COR versus face thickness for two alternative titanium alloys.
Figure 19:
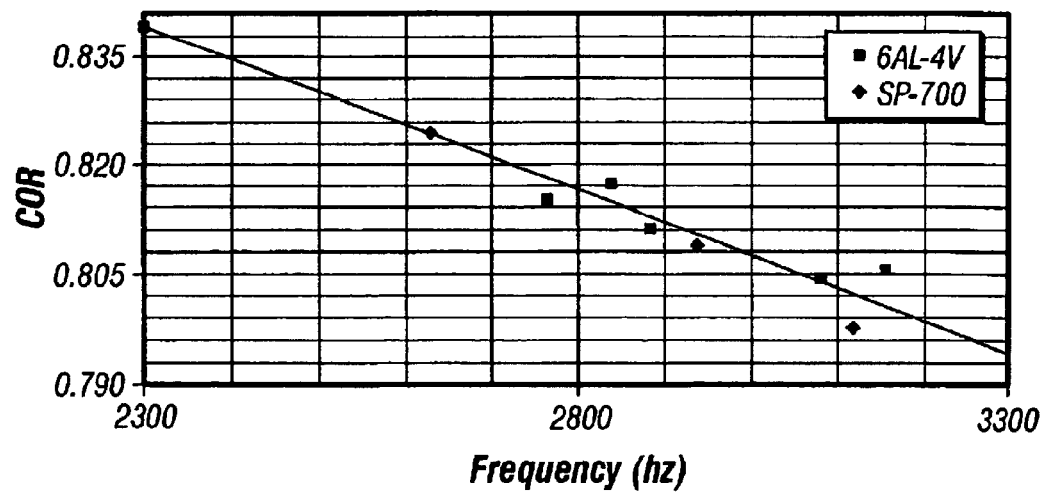
FIG. 19, is a graph of COR versus first resonant frequency for two alternative titanium alloys.

Several example club heads were produced with two commercially available titanium alloys 6AL-4V and SP700. The clubs were produced with a variety of uniform face thickness'. FIG. 18 illustrates that as face thickness is reduced for a given titanium alloy the COR increases in a linear fashion. However, different titanium alloys with slightly different moduli have distinct trend lines and thickness alone is insufficient to predict COR. FIG. 19 illustrates a plot of COR versus first primary resonant frequency for the same set of club heads as those of FIG. 18. FIG. 18 illustrates that first primary resonant frequency is predictive of COR regardless of titanium alloy. The first primary resonant frequency of a club head may be used as a quality control factor to ensure compliance with USGA COR rules.

While various descriptions of the present invention are described above, it should be understood that the various features of each embodiment can be used alone or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, the face and/or individual portions can have thickness variations in a step-wise or continuous fashion. Other modifications include a perimeter portion that has a thickness that is greater than or less than the adjacent, intermediate portion. In addition, the shapes of the central, intermediate, and perimeter portions are not limited to those disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A golf club head adapted for attachment to a shaft comprising:
   a face having a total face area and a first primary resonant frequency less than about 2900 Hz, the face comprising:
   a central zone having a first perimeter and a first flexural stiffness, wherein the central zone comprises between 15% and 60% of the total face area, and wherein the central zone includes a geometric center of the face;
   an intermediate zone surrounding the first perimeter of the central zone, the intermediate zone having a second flexural stiffness, wherein the first flexural stiffness of the central zone is at least 25,000 lb-in and greater than the second flexural stiffness of the intermediate zone; and
   a perimeter zone around the intermediate zone, wherein the area of the perimeter zone is up to 30% of the total face area.
   wherein the face exhibits a coefficient of restitution greater than or equal to 0.81.

2. The golf club head of claim 1, wherein the first flexural stiffness of the central zone is at least three times greater than the second flexural stiffness of the intermediate zone.

3. The golf club head of claim 2, wherein the first flexural stiffness of the central zone is at least six times greater than the second flexural stiffness of the intermediate zone.

4. The golf club head of claim 3, wherein the first flexural stiffness of the central zone is between six and twelve times greater than the second flexural stiffness of the intermediate zone.

5. The golf club head of claim 1, wherein the perimeter zone has a third flexural stiffness, and wherein the third flexural stiffness is at least two times greater than the second flexural stiffness.

6. The golf club head of claim 1, wherein the intermediate zone has an intermediate zone area being at least about 30% of the total face area.

7. The golf club head of claim 6, wherein the intermediate zone area is from about 30% to about 70% of the total face area.

8. The golf club head of claim 1, further comprising a shell defining an inner cavity with a volume of greater than about 250 cubic centimeters.

9. The golf club head of claim 1, wherein the face has a loft of greater than about 13°.

10. The golf club head of claim 2, wherein the central zone has a first thickness and the intermediate zone has a second thickness less than the first thickness, and wherein the central zone and the intermediate zone are made of the same material.

11. The golf club head of claim 2, wherein the central zone has a plurality of ribs on an inner surface thereof.

12. The golf club head of claim 1, wherein the club head has a center of gravity and a geometric center, and wherein the center of gravity is within 0.01 inch of the geometric center in a first horizontal direction between a heel and toe of the club head.

13. The golf club head of claim 12, wherein the center of gravity is within about 0.10 inch below the geometric center of the club in a vertical direction.

14. The golf club head of claim 13, wherein the center of gravity is less than about 1.25 inches from the geometric center of the club in a second horizontal direction toward a rear portion of the club head.

15. A golf club head adapted for attachment to a shaft comprising:
a face having a total face area and a first primary resonant frequency less than about 2900 Hz, the face comprising:
a central zone having a first perimeter and a first flexural stiffness, and a central zone area being at least 15% of the total face area, and the central zone including a geometric center of the face; and
an intermediate zone surrounding the first perimeter of the central zone, the intermediate zone having a second flexural stiffness, and the first flexural stiffness is at least 25,000 lb-in and greater than the second flexural stiffness.

16. The golf club head of claim 15, wherein the club head has a center of gravity and a geometric center,
wherein the center of gravity is within 0.01 inch of the geometric center in a first horizontal direction between a heel and toe of the club head,
wherein the center of gravity is within about 0.10 inch below the geometric center of the club in a vertical direction, and
wherein the center of gravity is less than about 1.25 inches from the geometric center of the club in a second horizontal direction toward a rear portion of the club head.

17. The golf club head of claim 15, wherein the second flexural stiffness is less than about 16,000 lb-in.

18. The golf club head of claim 15, wherein the face has a coefficient of restitution of greater than or equal to 0.81.

19. The golf club head of claim 15, wherein the first flexural stiffness is greater than about 55,000 lb-in.

20. The golf club head of claim 15, wherein the central zone has a first average thickness and the intermediate zone has a second average thickness and the first average thickness is greater than 1.5 times the second average thickness.

21. The golf club head of claim 15, further including a shell defining an inner cavity with a volume greater than about 250 cubic centimeters.

22. The golf club head of claim 15, wherein the face has a loft of greater than about 13°.

23. A golf club head adapted for attachment to a shaft comprising:
a face having a total face area, the face comprising:
a central zone having a first perimeter and a first flexural stiffness, wherein the central zone comprises a geometric center of the face, wherein the central zone comprises at least 15% of the total face area, and wherein upon ball impact the central zone exhibits a first deformation amount; and
an intermediate zone surrounding the first perimeter, wherein the intermediate zone has a second perimeter and a second flexural stiffness, wherein a ratio of the first flexural stiffness to the second flexural stiffness is at least 3, and wherein upon ball impact the intermediate zone exhibits a second deformation amount substantially greater than the first deformation amount.

24. The golf club head of claim 23, wherein the first flexural stiffness is at least six to twelve times greater than the second flexural stiffness.

25. The golf club head of claim 24, wherein the first flexural stiffness is about eight times greater than the second flexural stiffness.

26. The golf club head of claim 23, further comprising a perimeter zone surrounding the second perimeter of the intermediate zone, wherein the perimeter zone has a third thickness and a third flexural stiffness.

27. The golf club head of claim 26, wherein the central zone has a first thickness, and wherein the intermediate zone has a second thickness less than the first and third thicknesses.

28. The golf club head of claim 26, wherein the third flexural stiffness is at least two times greater than the second flexural stiffness.

* * * * *

UNITED STATES PATENT AND TRADEMARK OFFICE
CERTIFICATE OF CORRECTION

PATENT NO. : 6,960,142 B2
DATED : November 1, 2005
INVENTOR(S) : Laurent C. Bissonnette, Nicholas M. Nardacci and Raymond L. Poyner It is certified that error appears in the above-identified patent and that said Letters Patent is hereby corrected as shown below:

Title page,
Item [74], *Attorney, Agent, or Firm*, should read -- Swidler Berlin LLP --.

Signed and Sealed this

Twenty-seventh Day of December, 2005

JON W. DUDAS
*Director of the United States Patent and Trademark Office*